(12) United States Patent
Ogle et al.

(10) Patent No.: US 10,179,175 B2
(45) Date of Patent: Jan. 15, 2019

(54) ISATOIC ANHYDRIDE DERIVATIVES AND APPLICATIONS THEREOF

(71) Applicant: The University of North Carolina at Charlotte, Charlotte, NC (US)

(72) Inventors: Craig A. Ogle, Charlotte, NC (US); Anthony J. Fowler, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 15/848,750

(22) Filed: Dec. 20, 2017

(65) Prior Publication Data

US 2018/0110862 A1 Apr. 26, 2018

Related U.S. Application Data

(60) Division of application No. 15/331,196, filed on Oct. 21, 2016, now Pat. No. 9,867,883, which is a continuation-in-part of application No. PCT/US2015/011751, filed on Jan. 16, 2015.

(60) Provisional application No. 62/248,024, filed on Oct. 29, 2015, provisional application No. 61/983,900, filed on Apr. 24, 2014.

(51) Int. Cl.
| | |
|---|---|
| *A61K 9/00* | (2006.01) |
| *A61K 47/54* | (2017.01) |
| *C07D 265/26* | (2006.01) |
| *A61K 47/59* | (2017.01) |

(Continued)

(52) U.S. Cl.
CPC ............ *A61K 47/545* (2017.08); *A61K 47/59* (2017.08); *A61K 47/593* (2017.08); *A61K 49/0052* (2013.01); *C07D 265/26* (2013.01);

*C12N 15/115* (2013.01); *C12N 2310/16* (2013.01); *C12N 2310/351* (2013.01)

(58) Field of Classification Search
CPC ..................................................... A61K 47/945
See application file for complete search history.

(56) References Cited

U.S. PATENT DOCUMENTS

| | | |
|---|---|---|
| 2,150,968 A | 3/1939 | Guenther et al. |
| 3,346,327 A | 10/1967 | Koenig |

(Continued)

FOREIGN PATENT DOCUMENTS

| | | |
|---|---|---|
| WO | 2007/145940 A2 | 12/2007 |
| WO | 2012/076794 A1 | 6/2012 |

OTHER PUBLICATIONS

Chinese Office Action issued in Application No. 2015800341456 dated Apr. 17, 2018, with partial English translation.

(Continued)

*Primary Examiner* — Paul W Dickinson
(74) *Attorney, Agent, or Firm* — McDermott Will & Emery LLP

(57) ABSTRACT

Isatoic anhydride derivatives having an N-substituent which includes a quaternary ammonium group are useful for labeling and/or functionalizing a target material and/or for coupling materials together. The isatoic anhydride derivatives of the present disclosure can be advantageously water soluble, easily prepared and purified. Isatoic anhydride derivatives useful in the present disclosure preferably have at least one chemically reactive group or at least one binding group or at least one detectable label. Anthranilate derivatives made from the isatoic anhydrides derivatives or otherwise and kits including the isatoic anhydride derivatives are also disclosed.

20 Claims, 8 Drawing Sheets

(51) Int. Cl.
*A61K 49/00* (2006.01)
*C12N 15/115* (2010.01)

(56) References Cited

U.S. PATENT DOCUMENTS

2010/0035761 A1   2/2010  Weeks et al.
2013/0253179 A1   9/2013  Burr et al.

OTHER PUBLICATIONS

S. Mortmer et al., "A fast-acting reagent for accurate analysis of RNA secondary and tertiary structure by SHAPE chemistry," Journal of American chemical society, 2007, vol. 129, pp. 4144-4145.
International Search Report issued in Application No. PCT/US2015/011751 dated Apr. 29, 2015.
McDonald, Discovery of novel series of quinolone a7 nicotinic acetylcholine receptor agonists, Bioorganic & Medical chemistry Letters, 2013, 23, 1684-1688.

Scheme 13

BSA = Bovine Serum Albumin

Scheme 14

ISATOIC ANHYDRIDE DERIVATIVES AND APPLICATIONS THEREOF

CROSS-REFERENCE TO RELATED APPLICATION

This application is a divisional of U.S. patent application Ser. No. 15/331,196, filed Oct. 21, 2016, which claims the benefit of U.S. Provisional Application No. 62/248,024 filed Oct. 29, 2015 and which is a continuation-in-part of Application No. PCT/US2015/011751 filed Jan. 16, 2015, which claims the benefit of U.S. Provisional Application No. 61/983,900 filed Apr. 24, 2014 the entire disclosures of each of which are hereby incorporated by reference herein.

TECHNICAL FIELD

The present disclosure relates to isatoic anhydride derivatives having an N-substituent which includes a quaternary ammonium group and associated anthranilate derivatives and use of such derivatives for chemical coupling and for modifying the surface of materials.

BACKGROUND

It is often desirable to couple a compound to another compound or material for a variety of applications including labeling and/or functionalizing a target compound or material. Such coupling processes can be used to couple small molecules and/or macromolecules together. For example, a carbodiimide coupling scheme, such as a 1-ethyl-3-(3-dimethylaminopropyl)carbodiimide (EDC) and N-hydroxysulfosuccinimide (sulfo-NHS), can be used to couple two unique macromolecules including a carboxyl group or an amine group respectively, Isatoic anhydride (also known as 2H-3,1-Benzoxazine-2,4(1H)-dione) and derivatives thereof are generally used as intermediates in organic synthesis. However, they have also been used in coupling reactions and to modify materials. For example, WO2012076794A1 and U.S. Patent Application Publication 20130253179 disclose coupling isatoic anhydride or a derivative thereof to functionalize ribonucleic acid (RNA) on certain ribose portions of RNA. WO2007145940 discloses analyzing the structure of RNA molecules by labeling the molecules with N-methylisatoic anhydride. U.S. Pat. Nos. 3,346,327 and 2,150,968 disclose using isatoic anhydride and derivatives thereof for modifying wool and cellulose.

However, some coupling schemes require the use of expensive reagents and/or result in the formation of undesired side products which must be removed from the desired reaction product. In addition, some coupling reactions can be slow and/or are difficult to monitor and quantify in real time. Further, many of the coupling schemes including isatoic anhydride and derivatives thereof use non-aqueous reaction media which are generally less desirable.

Accordingly, a continuing need exists for compounds that can be used to label and/or functionalize a target compound or material and/or to couple compounds or materials together.

SUMMARY OF THE DISCLOSURE

Advantages of the present disclosure include isatoic anhydride derivatives having an N-substituent which includes a quaternary ammonium group and associated anthranilate derivatives. The isatoic anhydride derivatives and anthranilate derivatives can be used for a variety of applications including labeling and/or functionalizing a target material and/or for coupling materials together.

These and other advantages are satisfied, at least in part, by an isatoic anhydride derivative having an N-substituent which includes a quaternary ammonium group. Such isatoic anhydride derivatives can have the following formula:

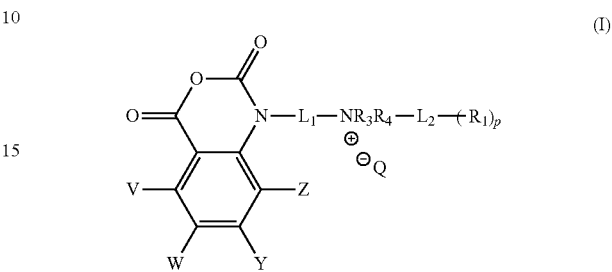

wherein V, W, Y, and Z individually represent H, $N_3$, $NO_2$, amino, alkylamino, dialkylamino, branched or linear alkyl, branched or linear alkenyl, branched or linear alkynyl, branched or linear alkoxy, branched or linear sulfenyl, an alkyne or azido substituted alkylamino, dialkylamino, alkyl, alkoxy, sulfenyl, formyl, acetyl, or halide; $L_1$ represents a linker group; $R_3$ and $R_4$ independently represent a linear or branched alkyl, an alkyl ether, or together form a cyclic heteroalkyl, or cyclic heteroaryl; $Q^-$ represents an anion; p is an integer from 0 to 2; when p is 0, $L_2$ represents a pendant organo group; when p greater than 0, $L_2$ represents a second independent linker group; $R_1$ represents a chemically reactive group, a binding group, or a detectable label.

Embodiments of isatoic anhydride derivative of the present disclosure include the following features individually or combined. For example, when p is 1, $L_2$ is a linker group and $R_1$ can be a chemically reactive group such as an azide, alkyne, protected thiol, a group including a disulfide moiety, alkene, arylalkene maleimide, acetal, aldehyde, ketone, ketal, hydrazone, epoxide, N-hydroxysuccinimide ester, a (sulfo)N-hydroxysuccinimide ester group, a thioester, a boronic acid, a boronic ester, or a trialkoxysilyl group; wherein V and Z can be H and W and Y can independently represents H, $N_3$, $NO_2$, $NH_2$, $NHR_5$, $NR_5R_5$, a $C_{1-6}$ alkyl, a $C_{1-6}$ alkenyl, an alkyne or azide substituted $NHR_5$, $NR_5R_5$, $C_{1-6}$, $OC_{1-6}$, $SC_{1-6}$, a $C_{1-6}$ alkynyl, —CHO or acetal; $R_3$ and $R_4$ can independently represent a $C_{1-6}$ alkyl or together form a 5-6 membered ring heterocycle; $R_5$ can represent $C_{1-8}$ aliphatic; $Q^-$ can be a halide anion e.g., Cl⁻, Br⁻ or I⁻; $L_1$ can be a di-radical $C_{1-60}$ organo; when p is greater than zero, $L_2$ represents a di-radical $C_{1-60}$ organo and when p is zero, $L_2$ represents a pendant $C_{1-60}$ organo. Alternatively, $L_1$ and $L_2$ can independently represent $R_5$, Ar, $R_5$–Ar, Ar—$R_5$, $R_5$—Ar—$R_5$, —(CH$_2$)n-, —(R$_5$O)m-(CH$_2$)n-, —(CH$_2$)n-(R$_5$O)m-R$_5$, —(CH$_2$)n-(OR$_5$)m-R$_5$, with or without heteroatoms along the main chain, and —(CH$_2$)n-(OR$_5$)m-XR$_5$, and —(CH$_2$)n$_1$-(OR$_5$)m$_1$-HA-(CH$_2$)n$_2$-(OR$_5$)m$_2$-R$_5$, wherein R$_5$ represents a $C_{1-8}$ aliphatic; Ar represents a di-radical aryl group; n, n$_1$ and n$_2$ independently represent integers of 1 to 30; m, m$_1$, and m$_2$ independently represent integers of 0 to 30; HA represents a group of heteroatoms such as —CO—, —C(O)X—, —XC(O)—, —X—, —S—, —S(O)—, —XS(O)$_2$—, —S(O)$_2$X—; and X represents O, S, NH, or NR$_5$ provided that if X is —NH—, the secondary amine does not substantially react with the anhydride of the isatoic anhydride derivative.

The isatoic anhydride derivatives of the present disclosure can be readily prepared from fragments thereof and methods for preparing the derivatives are provided.

Another aspect of the present disclosure includes a method of modifying a material by combining an isatoic anhydride derivative of the present disclosure with a material to form either (i) a isatoic anhydride derivative including the material coupled through $R_1$ having the structure of Formula (II) or (ii) an anthranilate derivative having the material coupled through the anhydride of the isatoic anhydride derivative having the structure of Formula (III):

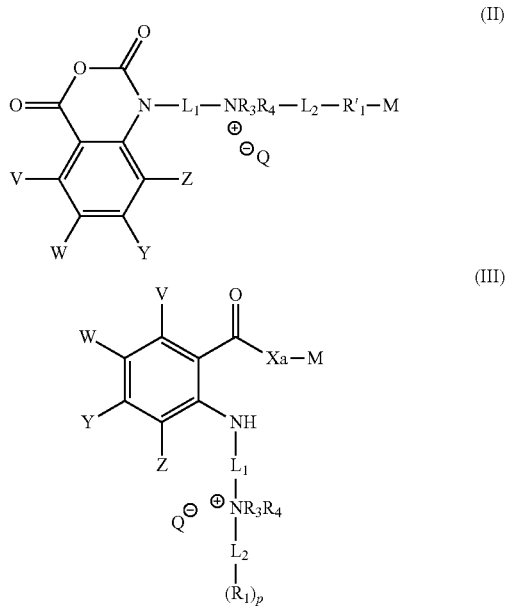

The variables V, W, Y, Z, $L_1$, $L_2$, $Q^-$, $R_3$, $R_4$, p and $R_1$ represent the same substituents as described for the derivatives of Formula (I) above including all of the various combinations and sub-combinations of each of the various variables. M represents a material and $R'_1$ represents a group formed from the reaction or interaction of $R_1$ and the material (M). Materials that are useful for the present disclosure include, for example, biological materials, polymers, functionalized materials, glass, ceramic, plastic, wood, textile, wool, paper, cellulose, metal, metal alloy, etc. The material can be in the size of a micro or nano-particle and in the shape of a flat sheet, a sphere, a rod, etc.

Another aspect of the present disclosure includes an anthranilate derivative according to Formula (III):

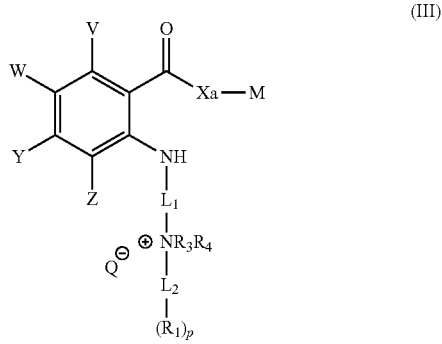

The variables V, W, Y, Z, $L_1$, $L_2$, $Q^-$, $R_3$, $R_4$, p, $R_1$, M and Xa, represent the same substituents as described above including all of the various combinations and sub-combinations of each of the various variables.

In some embodiments, an anthranilate of Formula (III) includes a biological material as the material, e.g., where M in Formula (III) represents "Bio". Such biological materials include, for example, RNA, an RNA aptamer, and a functionalized derivative thereof (e.g. Olaptesed pegol (NOX-A12) and Emapticap pegol (NOX-E36), Noxxon Pharma), DNA, a DNA aptamer, and a functionalized derivative thereof (e.g. anti-nucleolin aptamer AS1411), a protein (e.g., Streptavidin, Neutravidin, Avidin), a peptide (e.g., Arginine-Glycine-Aspartic Acid (RGD), cyclic-RGD etc.), a peptidomimetic (e.g., $\alpha_v\beta_3$ antagonist S247 etc.), an enzyme (e.g., Elspar (asparaginase)), a peptide aptamer, an antibody (Ab) (e.g., Herceptin® (Trastuzumab), Avastin® (bevacizumab), ERBITUX® (cetuximab) etc.), antibody fragment (e.g., antigen binding fragments (Fab) e.g. LUCENTIS® (ranibizumab), single chain variable fragments (scFv) and third generation 3G molecules), a sugar (Glucose, Glucosamine etc.), a starch, etc.

Another aspect of the present disclosure includes anthranilates having multiple functionalities, e.g., where M in Formula (III) represents $L_3$-$R''_1$ as shown in IIIB. Such anthranilates can have the following formula:

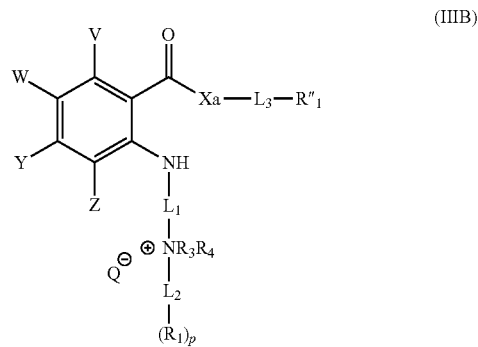

The variables V, W, Y, Z, $L_1$, $L_2$, $Q^-$, $R_3$, $R_4$, p and $R_1$ represent the same substituents as described for the derivatives of Formula (I) herein including all of the various combinations and sub-combinations of each of the various variables. HXa represents a $NH_2$, $NHR_5$, SH, or OH group, for example, and $L_3$ and $R''_1$ represent, respectively, the same groups as described for $L_1$ and $R_1$ of Formula (I) herein including all of the various combinations and sub-combinations of each of the various variables.

The anthranilate derivatives of the present disclosure can be readily prepared from fragments thereof and methods for preparing the derivatives are provided.

Another aspect of the present disclosure includes kits containing at least a first isatoic anhydride derivative having an N-substituent which includes a quaternary ammonium group. In some embodiments the isatoic anhydride derivative has at least one chemically reactive group or at least one binding group. In other embodiments, the kit contains a second isatoic anhydride derivative having an N-substituent which includes a quaternary ammonium group, wherein the first isatoic anhydride derivative includes a first chemically reactive group, and the second isatoic anhydride derivative includes a second chemically reactive group that can chemically react with the first chemically reactive group of the first isatoic anhydride derivative to couple the first and second isatoic anhydride derivatives.

Another aspect of the present disclosure includes isatoic anhydrides that can be used as multiplexing reagents such as isatoic anhydrides having one or more deuterium atoms substituted for one or more hydrogen atoms. Such multiplex isatoic anhydrides can be represented by the following formula:

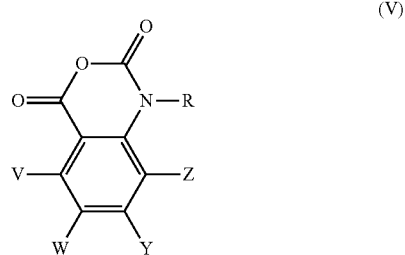

(V)

The variables V, W, Y, and Z represent the same substituents as described for the derivatives of Formula (I) herein including all of the various combinations and sub-combinations of each of the various variables. R represents an organo substituent having one or more hydrogen atoms substituted by one or more deuterium atoms.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

DETAILED DESCRIPTION OF THE DISCLOSURE

Figure 1:
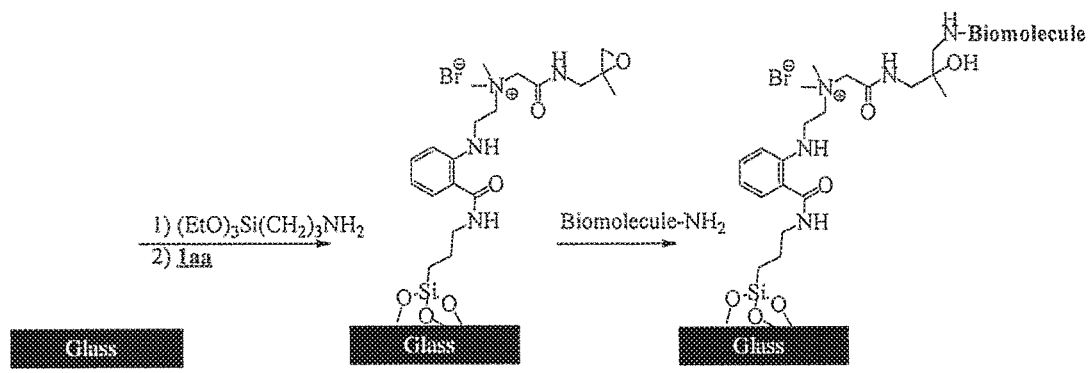
FIG. 1 is an illustration of modified surface of a substrate, e.g., a glass surface, with an isatoic anhydride derivative of the present disclosure.

The present disclosure relates to isatoic anhydride derivatives having an N-substituent which includes a quaternary ammonium group and associated anthranilate derivatives. These derivatives are useful for labeling and/or functionalizing a target material and/or for coupling materials together. The isatoic anhydride derivatives of the present disclosure can be advantageously water soluble. Water solubility of the isatoic anhydride derivative is promoted by the quaternary ammonium group on the compound. Water solubility can be advantageous when coupling the isatoic anhydride derivative in aqueous media, which is a preferred media for most biological chemistry. Further, certain of the isatoic anhydride derivatives of the present disclosure are readily prepared or derived from common commercial starting reagents and can be readily isolated from non-aqueous reaction media due to high polarity and low solubility n common organic solvents. In addition, anthranilates associated with the isatoic anhydride derivatives are provided as well as uses thereof.

Isatoic anhydride derivatives useful in the present can have the following formula:

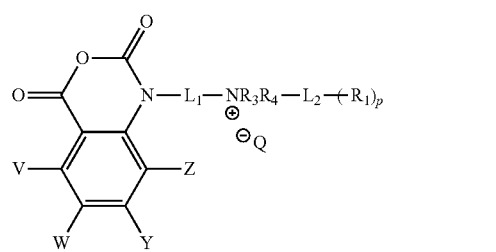

(I)

The variables V, W, Y, and Z independently represent H; $N_3$ (azido); $NO_2$ (nitro); amino; alkylamino; dialkylamino; branched or linear alkyl, e.g., a $C_{1-8}$ alkyl such as methyl, ethyl, propyl, isopropyl; branched or linear alkenyl, e.g., a $C_{1-8}$ alkenyl such as vinyl; branched or linear alkynyl, e.g., a $C_{1-8}$ alkynyl such as acetylenyl (—C≡CH); branched or linear alkoxy, such as methoxy, ethoxy; branched or linear sulfenyl, such as S—$C_{1-8}$; formyl (—CHO), acetyl (—$COR_5$), halide such as fluoro, chloro, bromo, iodo. In each case, the alkylamino, dialkylamino, alkyl, alkoxy and sulfenyl can be substituted with an alkynyl or azido group, such as $NHR_5$, alkyne or azido; $NR_5R_5$, alkyne or azido; $C_{1-8}$ alkyne or azido, $OC_{1-8}$ alkyne or azido; $SC_{1-8}$ alkyne or azido; $R_5$ represents $C_{1-8}$ aliphatic, which can be linear, branched, acyclic, cyclic, saturated or unsaturated. Aliphatic groups herein include linear, branched, acyclic, cyclic, saturated or unsaturated. $L_1$ represents a linker group, e.g., a di-radical organo group between the two nitrogen atoms. $R_3$ and $R_4$ independently represent a linear or branched alkyl, e.g., a $C_{1-8}$ alkyl such as methyl, ethyl, n-propyl, n-butyl, etc., an alkyl ether; or together form a cyclic heteroalkyl, such as a pyrrolidinyl, piperidinyl, morpholinyl, piperazinyl; or cyclic heteroaryl, such as pyridinyl, imidazoyl, etc. $Q^-$ represents an anion such as a halide, e.g., a fluoro, chloro, bromo, or iodo anion, a sulfonate, sulfate, or carboxylate anion. The variable p is an integer from 0 to 2, e.g., p can be 0, 1, or 2. When p is 0, the isatoic anhydride derivative does not include an $R_1$ group and $L_2$ represents a pendant organo group on the quaternary amine nitrogen. When p is greater than 0, $R_1$ is present and $L_2$ represents a second independent linker group, e.g., a di-radical organo group between the quaternary nitrogen and one or more $R_1$ groups. When p is 2, there are two $R_1$ groups on the isatoic anhydride derivatives, which can be the same or different.

As linker groups, $L_1$ and $L_2$ independently represent a di-radical organo group, e.g., a di-radical $C_{1-60}$ organo, which can be aliphatic or aromatic or include elements of both. The di-radical organo group can include heteroatoms along the main chain and/or substituents. As a pendant group, $L_2$ represents a pendant organo group, e.g., a pendant $C_{1-60}$ organo group, which can be aliphatic or aromatic or include elements of both. The pendant group can include heteroatoms along the main chain and/or substituents. Hereroatoms (HA) along the main chain of the linker di-radical or pendent organo group can include one or more of: —CO—, —C(O)X—, —XC(O)—, —X—, —S—, —S(O)—, —XS(O)$_2$—, —S(O)$_2$X—, wherein X is O, S, NH, or NR$_5$ provided that if X is —NH—, the secondary amine does not substantially react with the anhydride of the isatoic anhydride derivative. That is, the secondary amine is not basic by virtue of having an electron withdrawing substituent such as an aryl group or a secondary amine substituted with a dinitrophenyl. The di-radical organo group or pendent organo group having heteroatoms along the main chain include polyethers, e.g., polyethylene glycol, polypropylene glycol, poly(tetramethylene oxide) (also referred to as a polytetrahydrofuran), polyesters, polyamides, ethyloxazolines, etc. In addition, the di-radical organo group or pendent organo group of $L_1$ and $L_2$ can independently include substituents on or off the main chain such as an alkyl, aryl, alkoxy, thioether, amide, halide, etc.

If present, $R_1$ represents a chemically reactive group, a binding group, or a detectable label. For example, $R_1$ can be a chemically reactive group such as an azide, alkyne, protected thiol, a group including a disulfide moiety, such as a disulfide pyridine group, alkene, arylalkene such as a styrene group, maleimide, acetal, aldehyde, ketone, ketal, hydrazone, epoxide, N-hydroxysuccinimide ester, a (sulfo) N-hydroxysuccinimide ester group, a thioester, a boronic acid (B(OH)$_2$) group, a boronic ester (e.g., a B(OR$_6$)$_2$ group), a trialkoxysilyl group (e.g., a Si(OR$_7$)$_3$ group), where each R$_6$ can be the same or different and represents a linear or branched alkyl, e.g., a $C_{1-8}$ alkyl such as methyl, ethyl, n-propyl, n-butyl, etc., or an aryl or heteroaryl, or together form a cyclic alkyl, e.g., (—CH$_2$CH$_2$—), or a cyclic heteroalkyl, e.g., CH$_3$N(CH$_2$CH$_2$—)$_2$, O(CH$_2$CH$_2$—)$_2$, a cyclic aryl or cyclic heteroaryl; and where each R$_7$ can be the same or different and represents a linear or branched alkyl, e.g., a $C_{1-8}$ alkyl such as methyl, ethyl, n-propyl, n-butyl, etc.; or $R_1$ can be a binding group such as a biotin group or a hapten such as a 2,4-dinitrophenyl; or $R_1$ can be a detectable label such as a dye, fluorophore or radiolabel. Isatoic anhydride derivatives useful in the present disclosure preferably have at least one chemically reactive group or at least one binding group or at least one detectable label.

In one aspect of the present disclosure, V, W, Y, and Z, independently represent hydrogen, an amino, alkylamino, dialkylamino, a nitro, an azido, a $C_{1-6}$, alkyl, alkenyl or alkynyl, an alkyne or azido substituted NHR$_5$, NR$_5$R$_5$, $C_{1-6}$, SC$_{1-6}$, a formyl, or an acetal. In an embodiment, V and Z are H and W and Y independently represents H, N$_3$, NO$_2$, NH$_2$, NHR$_5$, NR$_5$R$_5$, a $C_{1-6}$ alkyl, a $C_{1-6}$ alkenyl such as —CH=CH$_2$, a $C_{1-6}$ alkynyl such as —C≡CH, alkyne or azido substituted NHR$_5$, alkyne or azido substituted NR$_5$R$_5$, alkyne or azido substituted OC$_{1-6}$, alkyne or azido substituted SC$_{1-6}$, —CHO or acetal. In another embodiment, V, Y, and Z can be H and W can be H, N$_3$, NO$_2$, NH$_2$, NHR$_5$, NR$_5$R$_5$, a $C_{1-6}$ alkyl, a $C_{1-6}$ alkenyl such as —CH=CH$_2$, a $C_{1-6}$ alkynyl such as —C≡CH, —CHO or acetal. $R_3$ and $R_4$ independently represent a $C_{1-6}$ alkyl or together form a 5-6 membered ring heterocycle, such as a pyrrolidinyl. $Q^-$ represents a halide. $L_1$ represents a di-radical $C_{1-30}$ organo, e.g., a di-radical $C_{1-20}$ organo, which can be aliphatic or aromatic or include elements of both and which can include heteroatoms along the main chain and/or substituents as described above. $L_2$ represents a $C_{1-30}$ organo, e.g., a $C_{1-20}$ organo, which can be aliphatic or aromatic or include elements of both and which can include heteroatoms along the main chain and/or substituents as described above. When P is 0, $L_2$ is a di-radical $C_{1-30}$ organo, e.g., a di-radical $C_{1-20}$ organo and when P is 1, $L_2$ is a pendant $C_{1-30}$ organo, e.g., a pendant $C_{1-20}$ organo. In an embodiment, $L_1$ and $L_2$ independently represent $C_{1-30}$ alkyl, aryl, $C_{2-30}$ ether, polyether, or some combination thereof and can further include one or more or none of esters, amides, tertiary amines, aryls and heteroaryl groups along the main chain or pendent thereon, e.g., $L_1$ and $L_2$ independently represent R$_5$, Ar, R$_5$—Ar, Ar—R$_5$, R$_5$—Ar—R$_5$, —(CH$_2$)n-, —(R$_5$O)m-(CH$_2$)n-,—(CH$_2$)n-(R$_5$O)m-R$_5$, —(CH$_2$)n-(OR$_5$)m-R$_5$, with or without heteroatoms along the main chain, and —(CH$_2$) n-(OR$_5$)m-XR$_5$, and —(CH$_2$)n$_1$-(OR$_5$)m$_1$-HA-(CH$_2$)n$_2$-(OR$_5$)m$_2$-R$_5$, wherein X, R$_5$, and heteroatoms (HA) are as defined above; Ar represents a di-radical aryl group such as a phenylene; n, n1 and n2 independently represent integers of 1 to 30, e.g., 1 to 8 and preferably 1 to 6; m, m1, and m2 independently represent integers of 0 to 30, e.g., 0 to 8 and preferably 0 to 6.

Additional examples of isatoic anhydride derivatives having an N-substituent which includes a quaternary ammonium group are provided in Table 1 below.

TABLE 1

No. —L$_1$—R$_3$R$_4$Q$^-$+N—L$_2$—(R$_1$)p

1 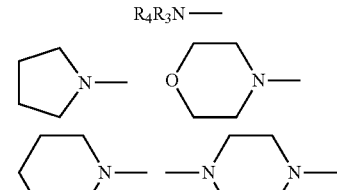

2 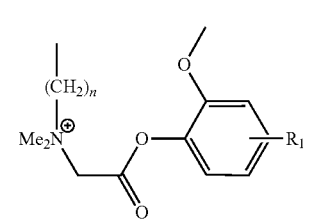

TABLE 1-continued
| No. | —L₁—R₃R₄Q⁻⁺N—L₂—(R₁)p |
|---|---|
| | R₁ is —CH₂—(epoxide), —CH₂—(methyl epoxide), or —CHO |
| 3 | 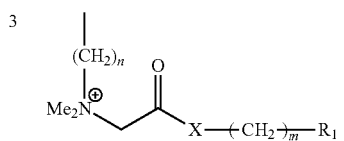 |
| | R₁ is —CH₂—(epoxide), —CH₂—(methyl epoxide), or —CHO |
| | X is NH, NR₅, S, O |
| 4 | 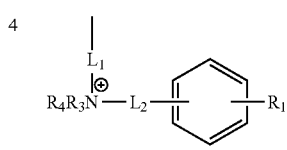 |
| | 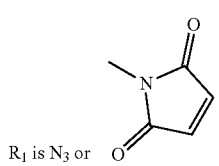 |
| | R₁ is N₃ or (N-methylmaleimide) |
| 5 | 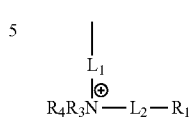 |
| | R₁ is N₃, —C≡CH, —C≡CR₅, —C≡CH, —C≡CR₅, or |
| | 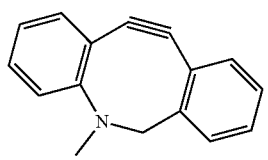 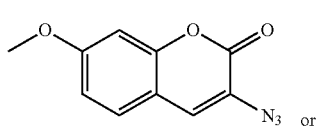 [SMILES: COc1ccc2cc(N=[N+]=[N-])c(=O)oc2c1 ; "or"] or —X— (2,4-dinitrophenyl) |
| | 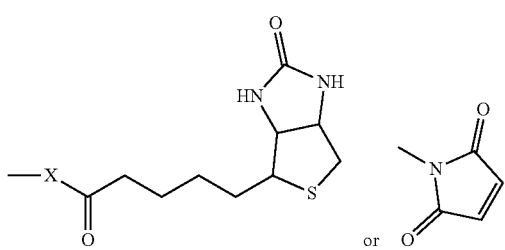 |
| | X = NH, NR₅, S, O |
| 6 | 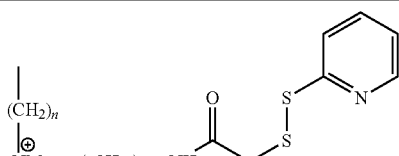 |
| 7 | 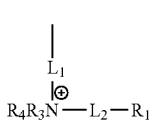 |
| | 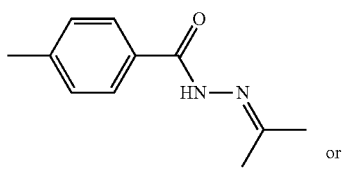 |
| | R₁ is or 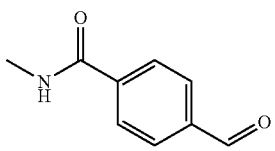 |
| 8 | 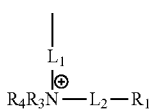 |
| | R₁ is 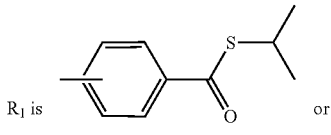 or |
| | 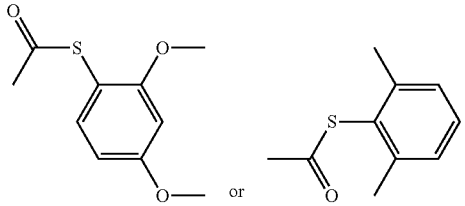 |
| 9 | 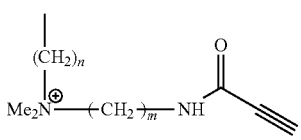 |
| 10 | 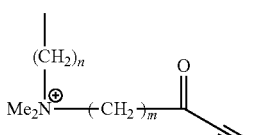 |
| 11 | 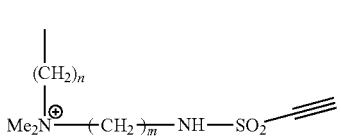 |

TABLE 1-continued

No. —L$_1$—R$_3$R$_4$Q$^{-+}$N—L$_2$—(R$_1$)p

| 12 | 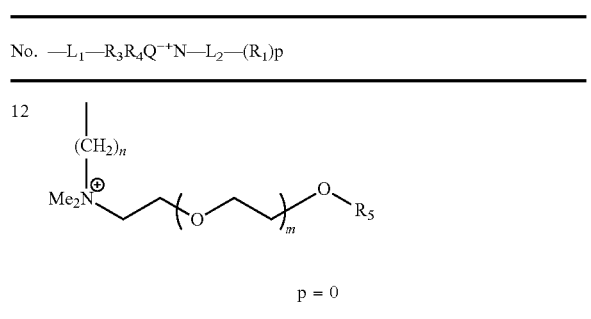 |
|---|---|
|  | p = 0 |

The variables of V, W, Y, Z, Q$^-$, and R$_5$ for the compounds and formulae in Table 1 are as defined earlier. The variable n represents an integer of 1 to 30, e.g., 1 to 8 and preferably 1 to 6 and m represents an integer of 0 to 30, e.g., 0 to 8 and preferably 0 to 6, in an embodiment, Formulae 4, 5, 7, or 8 in Table 1 have R$_3$ and R$_4$ independently represent a C$_{1-6}$ alkyl or together form a 5-6 membered ring heterocycle, such as a pyrrolidinyl; and L$_1$ and L$_2$ independently represent —R$_5$—, —(CH$_2$)n-, —(R$_5$O)m-(CH$_2$)n-, —(CH$_2$)n-(R$_5$O)m-R$_5$—, —(CH$_2$)n-(OR$_5$)m-R$_5$—, with or without heteroatoms along the main chain, and —(CH$_2$)n-(OR$_5$)m-XR$_5$—, —(CH$_2$)n$_1$-(OR$_5$)m$_1$-HA-(CH$_2$)n$_2$-(OR$_5$)m$_2$-R$_5$—, wherein X, R$_5$, and heteroatoms (HA) are as defined above; n, n1 and n2 independently represent integers of 1 to 30, e.g., 1 to 8 and preferably 1 to 6; m, m1, and m2 independently represent integers of 0 to 30, e.g., 0 to 8 and preferably 0 to 6. Additional embodiments of the compounds and formulae in Table 1 include, independently or in any combination, wherein V and Z are H and W and Y independently represents H, N$_3$, or NO$_2$, or wherein V, Y, Z each represent H and W represents H, N$_3$, or NO$_2$; Q$^-$ represents a halide, e.g., Cl$^-$, Br$^-$ or I$^-$.

The isatoic anhydride derivatives of the present disclosure can be readily prepared from common starting materials. For example, the isatoic anhydride derivatives of the present disclosure can be prepared generally according to either Scheme 1 or Scheme 2 shown below.

Scheme 1

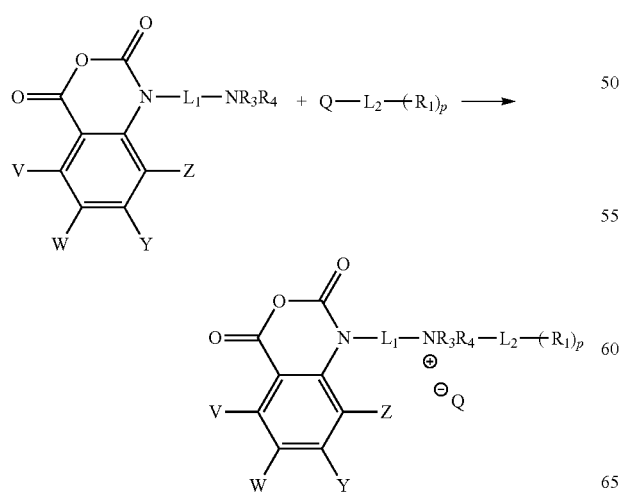

Scheme 2

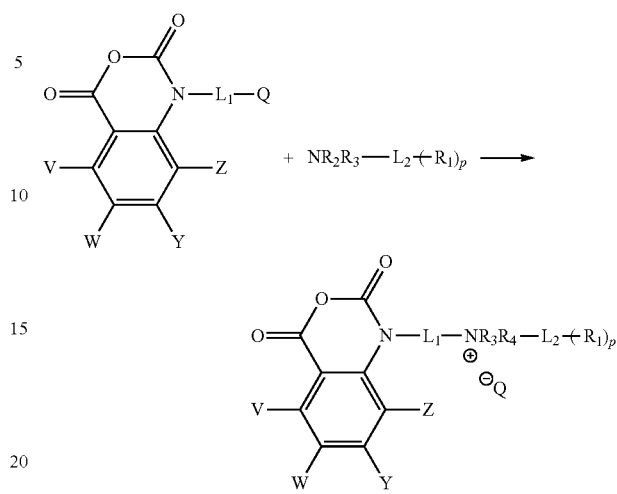

As shown in Scheme 1, isatoic anhydride derivatives can be prepared by reacting an isatoic anhydride amine with a Q-L$_2$-(R$_1$)p compound. Alternatively, and as shown in Scheme 2, isatoic anhydride derivatives can be prepared by reacting a Q-substituted isatoic anhydride with an amine compound. The procedures shown in Schemes 1 and 2 offer versatile processes for preparing the isatoic anhydride derivatives of the present disclosure.

In one embodiment of the present disclosure, V, W, Y, Z are H, L$_1$ is —(CH$_2$)$_2$—, R$_3$ and R$_4$ are methyl, p is 1 and the isatoic anhydride derivatives can be prepared according to the following procedure.

Method A

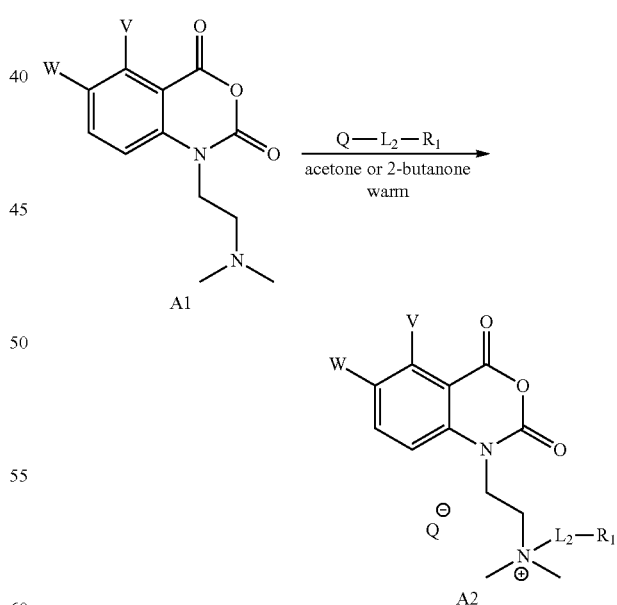

Method A can be carried out by combining equimolar amounts A1 and QL$_2$R$_1$ in a reaction flask. Enough of a solvent, such as acetone, can be added to the reaction flask to just dissolve the two reactants. The flask can be capped and the mixture warmed to about 40-45° C. to encourage the reaction. Many of the isatoic anhydride derivatives prepared by this Method A result in crystalline compounds which can be filtered to remove solvent and unreacted starting materials. The isatoic anhydride derivatives prepared by this Method A can also be encouraged to form crystalline compounds by adding a non-solvent such as diethyl ether. Non-crystalline derivatives can be purified by chromatography. Sluggish reactions can use different solvents, such as 2-butanone, and the reaction mixture warmed to about 60° C. Additionally, a catalytic amount of NaI can be added to accelerate the reaction. Products that are soluble in acetone can be purified by column chromatography. For example, the following isatoic anhydride derivatives A2 can be prepared from the following readily available or readily derivable starting materials and compound A1 using Method A.

TABLE 2

| QL$_2$R$_1$ | Group —L$_2$R$_1$ on A2 | Derivative |
|---|---|---|
| (CAS #305-12-4) | | 13 |
| Can be prepared from alkene (CAS # 305-12-4) by by ozonolysis followed by dimethylsulfide | | 14 |
| Can be prepared from the alkene (CAS #305-12-4) by treatment with m-chloroperbenzoic acid | | 15 |
| (CAS #132426-20-1) | | 16 |
| Can be prepared from the alkene (CAS #132426-20-1) by treatment with m-chloroperbenzoic acid | | 17 |
| (CAS #1596716-75-4) | | 18 |

TABLE 2-continued
| QL₂R₁ | Group —L₂R₁ on A2 | Derivative |
|---|---|---|
| 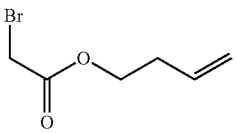 (CAS #90449-03-9) | 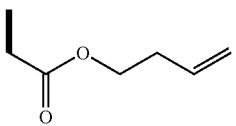 | 19 |
| 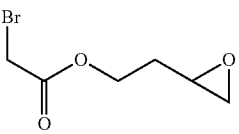 (CAS #1333418-55-5) | 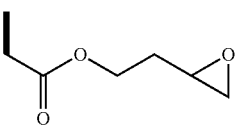 | 20 |
| 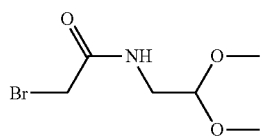 (CAS#1225772-58-6) | 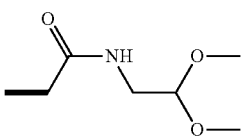 | 21 |
| 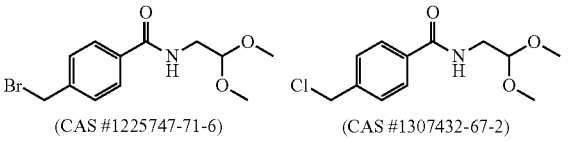 (CAS #1225747-71-6)    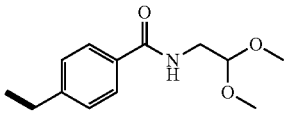 (CAS #1307432-67-2) | 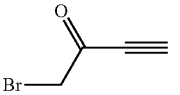 | 22 |
| 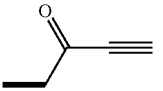 (CAS #449204-48-2) | 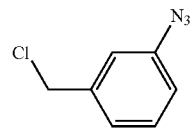 | 23 |
| 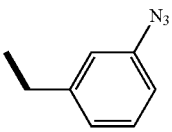 (CAS #120692-80-0) |  | 24 |
| 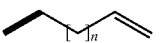 n = 1 (CAS #7766-51-0); n = 2 (CAS #7766-48-5); n = 3 (CAS #18922-04-8); n = 4 (CAS #107175-49-5) | 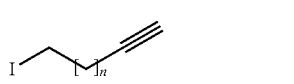 | 25 |
| 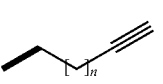 n = 1 (43001-25-8); n = 2 (2468-55-5); n = 3 (2468-56-6); n = 4 (87462-66-6) | 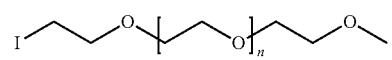 | 26 |
| 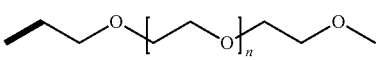 Can be prepared from the corresponding alcohol by treating with N-iodosuccinimide and triphenylphosphine | 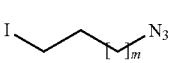 | 27 |
| 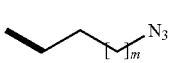 m = 2 (CAS #42059-30-3); m = 3 (CAS #58503-62-1); m = 4 (CAS #148759-55-1); m = 5 (CAS #142523-71-5) | | 28 |

TABLE 2-continued
| QL₂R₁ | Group —L₂R₁ on A2 | Derivative |
|---|---|---|
| 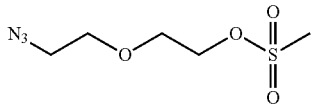 CAS #176520-23-3 | 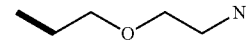 | 29 |
| 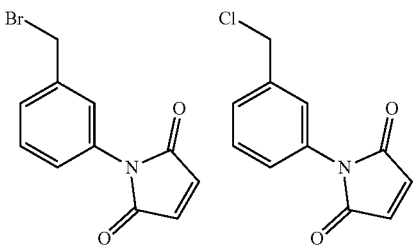 (CAS #256517-22-3)  (CAS #256517-21-2) | 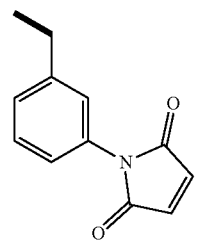 | 30 |
| 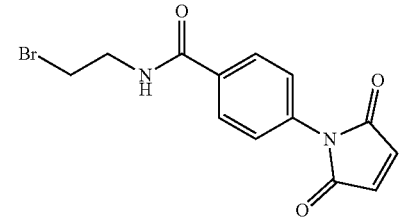 Can be prepared from CAS # 60693-33-6 in 2 steps by reacting with thionyl chloride followed by 2-bromoaminoethane (CAS #2576-47-8) | 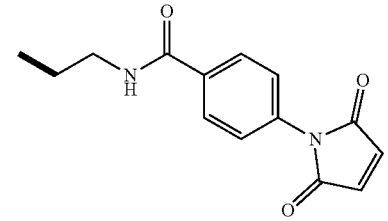 | 31 |
| 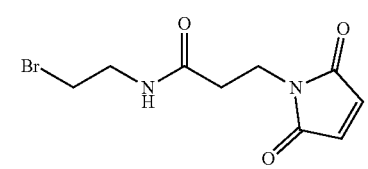 Can be prepared from CAS # 5724-76-5 in 2 steps by reacting with thionyl chloride followed by 2-bromoaminoethane (CAS #2576-47-8) | 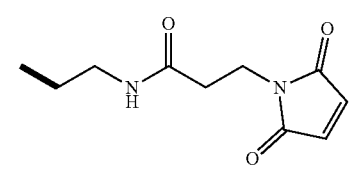 | 32 |
| 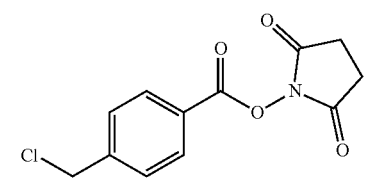 (CAS #65190-50-3) | 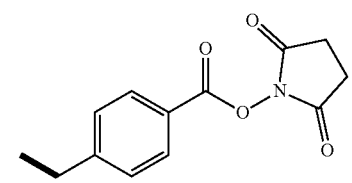 | 33 |
| 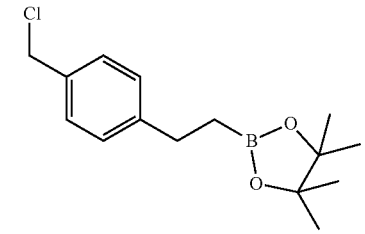 Can be prepared by reacting the boronic acid (CAS #1557160-06-1) with pinacol and MgSO₄ | 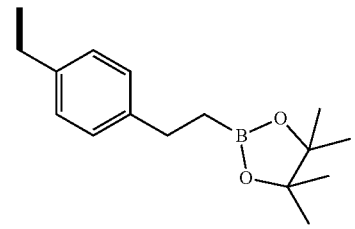 | 34 |

In another embodiment of the present disclosure, V, W, Y, Z are H, $L_1$ is —$(CH_2)_3$—, p is 1 and the isatoic anhydride derivatives can be prepared according to the following procedure.

Method B

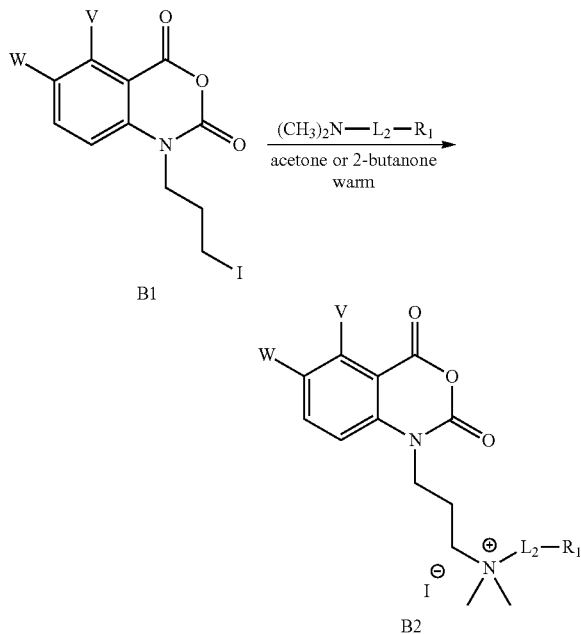

Method B can be carried out by combining equimolar amounts B1 and $(CH_3)_2NL_2R_1$ in a reaction flask. Enough of a solvent, such as acetone, can be added to the reaction flask to just dissolve the two reactants. The flask can be capped and the mixture is warmed to about 40-45° C. to encourage the reaction. Many of the isatoic anhydride derivatives prepared by this Method B result in crystalline compounds which can be filtered to remove solvent and unreacted starting materials. The isatoic anhydride derivatives prepared by this Method B can also be encouraged to form crystalline compounds by adding a non-solvent such as diethyl ether. Non-crystalline derivatives can be purified by chromatography. Sluggish reactions can use different solvents, such as 2-butanone, and the reaction mixture warmed to about 60° C. Products that are soluble in acetone can be purified by column chromatography. For example, the following isatoic anhydride derivatives B2 can be prepared from the following readily available or readily derivable starting materials and compound B1 using Method B.

TABLE 3

| $(CH_3)_2NL_2R_1$ | Group —$L_2R_1$ on B2 | Derivative |
|---|---|---|
| ![structure: HC≡C-C(O)-NH-CH2CH2CH2-N(CH3)2]  Can be prepared from the acid chloride (CAS # 50277-65-1) by reacting with $(CH_3)_2NCH_2CH_2CH_2NH_2$ | ![structure: HC≡C-C(O)-NH-propyl] | 35 |
| ![structure: HC≡C-SO2-NH-CH2CH2CH2-N(CH3)2]  Can be prepared from the sulfonyl chloride (CAS # 519159-52-5) by reacting with $(CH_3)_2NCH_2CH_2CH_2NH_2$ | ![structure: HC≡C-SO2-NH-propyl] | 36 |
| ![structure: 4-O2N,2-O2N-phenyl-O-CH2CH2CH2-N(CH3)2]  (CAS #78328-22-0) | ![structure: 4-O2N,2-O2N-phenyl-O-propyl] | 37 |
| ![structure: 4-O2N,2-O2N-phenyl-NH-CH2CH2-N(CH3)2]  (CAS #4119-48-6) | ![structure: 4-O2N,2-O2N-phenyl-NH-ethyl] | 38 |

TABLE 3-continued

| (CH₃)₂NL₂R₁ | Group —L₂R₁ on B2 | Derivative |
|---|---|---|
| [structure] Can be prepared from the ester (CAS #956427-71-7) in 2 steps by treatment with hydrazine hydrate followed by reaction with acetone | [structure] | 39 |
| [structure] Can be prepared in one step from reaction of the thiol (CAS #63517-85-1) and 2,2'-dipyridyl disulfide (CAS #2127-03-9) | [structure] | 40 |
| [structure] Can be prepared in 2 steps by reaction of azidophenol (CAS #24541-43-3) with CDI (CAS # 530-62-1) and then subsequent treatment with (CH₃)₂NCH₂CH₂CH₂NH₂ | [structure] | 41 |
| [structure] (CAS #1048919-69-2) | [structure] | 42 |
| (H₃CO)₃Si–––N(CH₃)₂ CAS #2530-86-1 | (H₃CO)₃Si––– | 43 |
| [structure] Can be prepared by the hydrazide (CAS #863646-40-6) and acetone. | [structure] | 44 |

TABLE 3-continued

| (CH$_3$)$_2$NL$_2$R$_1$ | Group —L$_2$R$_1$ on B2 | Derivative |
|---|---|---|
| [structure] Can be prepared in a one pot reaction from the amide (CAS #1446017-37-3) by deprotonation with sodium hydride in DMF and subsequently adding Me$_2$NCH$_2$CH$_2$Cl. | [structure] | 45 |
| [structure] Can be prepared in a one pot reaction from the aniline (CAS # 1369862-03-2) by deprotonation with sodium hydride in DMF and subsequently adding Me$_2$NCH$_2$CH$_2$Cl. | [structure] | 46 |
| [structure] Can be prepared in 4 steps from the carboxylic acid of the Boc protected allythioether of cysteine (CAS #12773-55-3) by activation with EDCI followed by reaction with Me$_2$N(CH$_2$)$_3$NH$_2$. After removal of the Boc group, the acid chloride of the aromatic azide (CAS #14848-01-2) can be added to give the reactant above. | [structure] | 47 |

TABLE 3-continued

| (CH₃)₂NL₂R₁ | Group —L₂R₁ on B2 | Derivative |
|---|---|---|
| 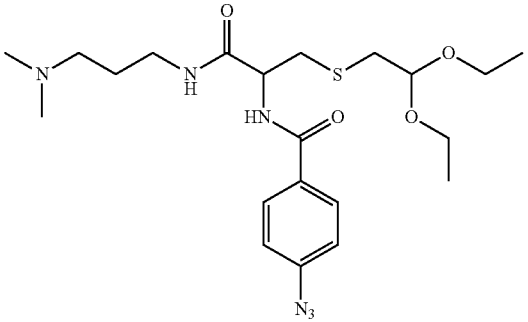 [SMILES: CCOC(CSCC(NC(=O)c1ccc(N=[N+]=[N-])cc1)C(=O)NCCCN(C)C)OCC] | 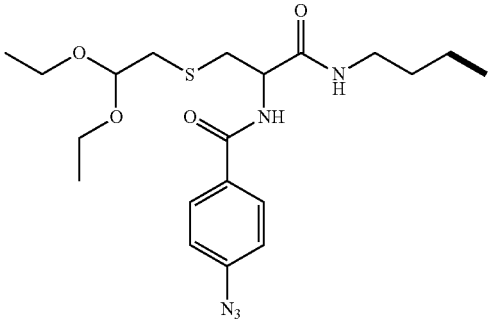 | 48 |
| Can be prepared in 4 steps from the carboxylic acid of the Boc protected acetal of cysteine (CAS #256656-38-9) by activation with EDCI followed by reaction with Me₂N(CH₂)₃NH₂. After removal of the Boc group, the acid chloride of the aromatic azide (CAS #14848-01-2) can be added to give the above reactant. | | |
| 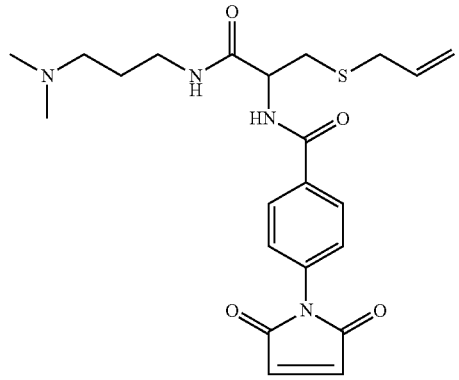 [SMILES: C=CCSCC(NC(=O)c1ccc(N2C(=O)C=CC2=O)cc1)C(=O)NCCCN(C)C] | 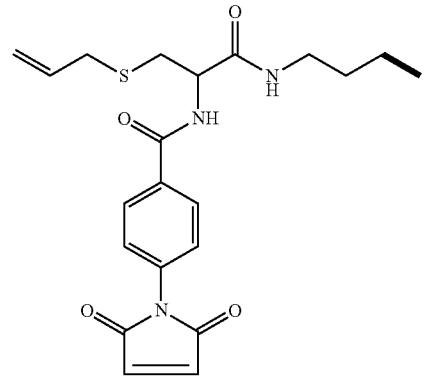 | 49 |
| Can be prepared in 4 steps from the carboxylic acid of the Boc protected allythioether of cysteine (CAS #12773-55-3) by activation with EDCI followed by reaction with ME₂N(CH₂)₃NH₂. After removal of the Boc group, the acid chloride of the aromatic maleimide (CAS #29305-46-2) can be added to give the above reactant. | | |
| 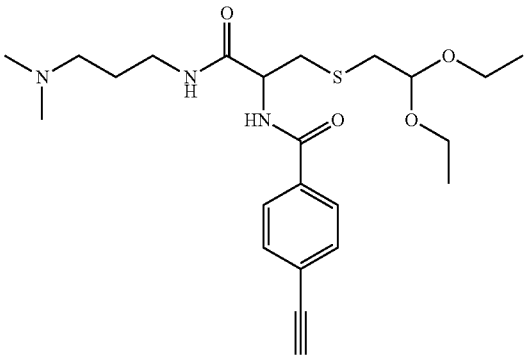 [SMILES: C#Cc1ccc(C(=O)NC(CSCC(OCC)OCC)C(=O)NCCCN(C)C)cc1] | 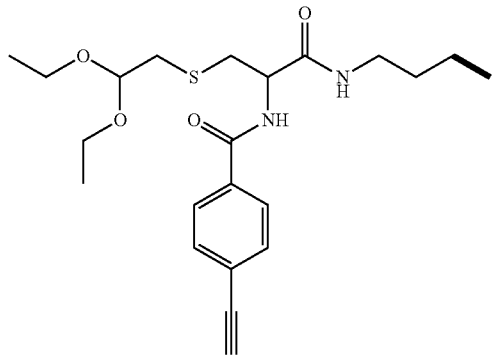 | 50 |
| Can be prepared in 4 steps from the carboxylic acid of the Boc protected acetal of cysteine (CAS #256656-38-9) by activation with EDCI followed by reaction with Me₂N(CH₂)₃NH₂. After removal of the Boc group, the acid chloride of the aromatic alkyne (CAS #62480-31-3) can be added to give the above reactant. | | |

TABLE 3-continued

| (CH₃)₂NL₂R₁ | Group —L₂R₁ on B2 | Derivative |
|---|---|---|
| 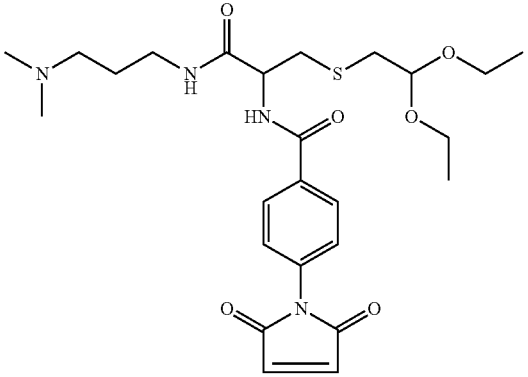 [SMILES: CCOC(CSCC(NC(=O)c1ccc(N2C(=O)C=CC2=O)cc1)C(=O)NCCCN(C)C)OCC] | 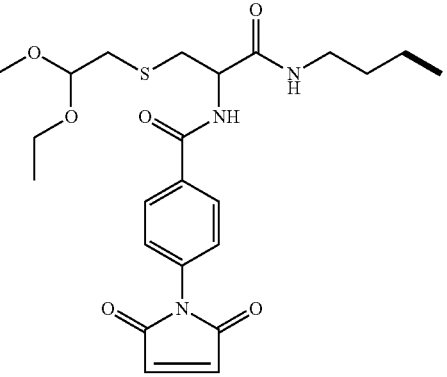 | 51 |
| Can be prepared in 4 steps from the carboxylic acid of the Boc protected acetal of cysteine (CAS #256656-38-9) by activation with EDCI followed by reaciton with Me₂N(CH₂)₃NH₂. After removal of the Boc group, the acid chloride of the aromatic maleimide (CAS #29305-46-2) can be added to give the reactant pictured above. | | |
| 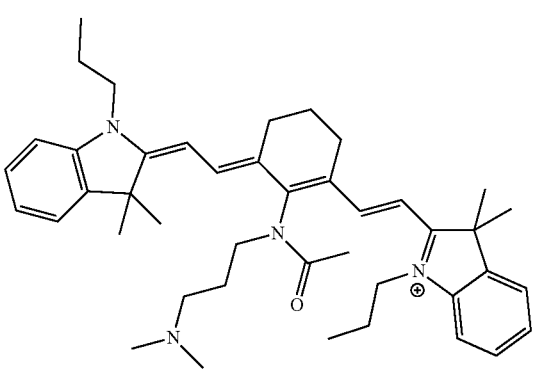 [SMILES: CCCN1/C(=C/C=C2\CCCC(/C=C/C3=[N+](CCC)c4ccccc4C3(C)C)=C2N(CCCN(C)C)C(C)=O)C(C)(C)c2ccccc21] | 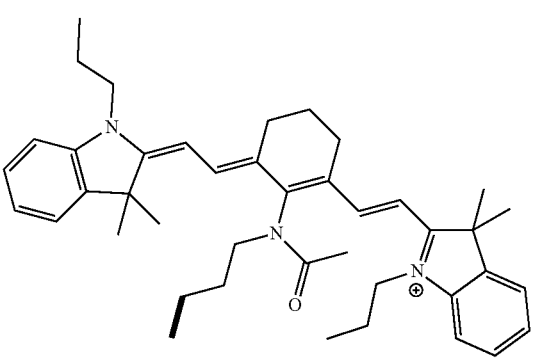 | 52 |
| CAS # 1255954-83-6 (a near-infrared dye) | | |
| 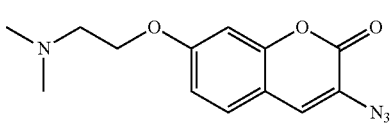 [SMILES: CN(C)CCOc1ccc2cc(N=[N+]=[N-])c(=O)oc2c1] | 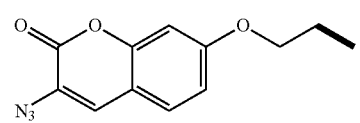 | 53 |
| Can be prepared from the phenol (CAS #817637-68-9) by deprotonation with sodium hydride in DMF and subsequently adding Me₂NCH₂CH₂Cl | | |
| 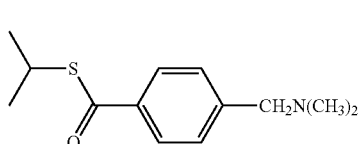 | 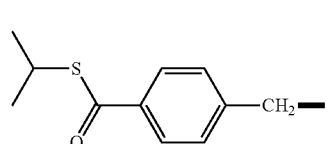 | 54 |
| Can be prepared from the acid chloride (CAS #121811-18-5) and isopropyl thiol | | |

TABLE 3-continued

| $(CH_3)_2NL_2R_1$ | Group —$L_2R_1$ on B2 | Derivative |
|---|---|---|
| (structure) Can be prepared from the acid chloride (CAS #127527-22-4) and the corresponding thiophenol (CAS#18906-37-1) | (structure) | 55 |
| (structure) Can be prepared from the acid chloride (CAS#949014-22-6) and the corresponding thiophenol (CAS#118-72-9) | (structure) | 56 |

The isatoic anhydride derivatives of the present disclosure, including those of the various tables, can be prepared in an analogous manner to the derivatives prepared by either Method A or Method B. Further the starting compounds of A1 and B1 can be readily prepared from the following readily available or readily derivable starting materials according to Method C or Method D, respectively, as shown below.

Method C

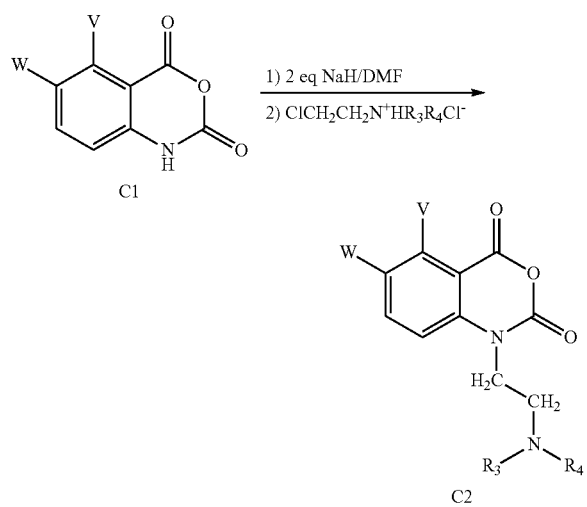

Method C can be carried out in an inert atmosphere, e.g., a nitrogen atmosphere. in this procedure, compound C1 can be dissolved in dry dimethylformamide (DMF) and 2 equivalents of sodium hydride can be added. The addition of sodium hydride can be such that it avoids foaming. Alternatively, potassium carbonate can be used in place of sodium hydride. The amine hydrochloride salt ($ClCH_2CH_2N^+HR_3R_4Cl^-$) can then be added. The product can be obtained by adding the reaction mixture to ice water and filtering off the product or by extraction. Analogously, a pegylated amine hydrochloride salt (e.g., $ClCH_2CH_2O(CH_2CH_2O)$ $nCH_2CH_2N^+HR_3R_4Cl^-$) can be used in place of amine hydrochloride salt ($ClCH_2CH_2N^+HR_3R_4Cl^-$). For example, the following starting isatoic anhydrides C2 can be prepared from the following readily available or readily derivable starting materials and compound C1 using Method C.

TABLE 4

| $ClCH_2CH_2N^+HR_3R_4Cl^-$ (CAS #) | Product C2 —$NR_3R_4$ |
|---|---|
| (structure) (CAS #7250-67-1) | (structure) |
| (structure) (CAS #18994-78-0) | (structure) |
| (structure) (CAS #1226896-29-2) | (structure) |
| (structure) (CAS #3647-69-6) | (structure) |

TABLE 4-continued

| ClCH$_2$CH$_2$N$^+$HR$_3$R$_4$Cl$^-$ (CAS #) | Product C2 ━NR$_3$R$_4$ |
|---|---|
| (CAS #126055-32-1) | |
| (CAS # 869-24-9) | |

Method D can be carried out in an inert atmosphere, e.g., a nitrogen atmosphere. In this procedure, compound D1 can be dissolved in dry DMF and sodium hydride can be added. The addition of sodium hydride can be such that it avoids foaming. The chloroiodo compound (CL-L$_1$-I) can then be added. When the reaction is complete the DMF can be removed from the reaction mixture with heat and vacuum, during the heating and removal of DMF the iodide exchanges for the chloride. The residue can be suspended/dissolved in THF. The product can be obtained by adding the slurry to ice water and filtering off the solid product or by the extraction of a liquid product into an organic phase.

Method D

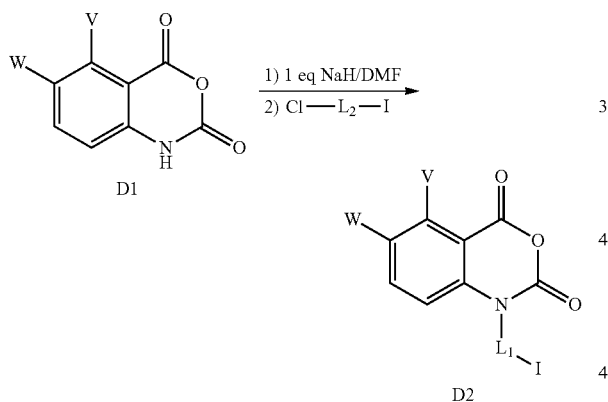

For example, the following starting isatoic anhydrides D2 can be prepared from the following readily available or readily derivable starting materials and compound D1 using Method D.

TABLE 5

| Cl-R-I (CAS #) | Product D2 —L$_1$—I |
|---|---|
| (CAS #10297-05-9) | |
| (CAS #60274-60-4) | |
| (CAS #34683-73-3) | |

TABLE 5-continued

| Cl-R-I (CAS #) | Product D2 —L$_1$—I |
|---|---|
| (CAS #42070-18-8) | |
| (CAS #42070-19-9) | |

The isatoic anhydride derivative of the present disclosure can be used for a variety of applications. In one aspect of the present disclosure, isatoic anhydride derivatives having an N-substituent which includes a quaternary ammonium group and further having at least one chemically reactive group or at least one binding group can be used to modify a material. That is, isatoic anhydride derivatives of the present disclosure can be used to label and/or functionalize a target material and/or to couple materials together.

In one aspect, isatoic anhydride derivatives of the present disclosure can be combined with a material to form either (i) a isatoic anhydride derivative including the material coupled through R$_1$ having the structure of Formula (II) or (ii) an anthranilate derivative having the material coupled through the anhydride of the isatoic anhydride derivative having the structure of Formula (III) as shown below:

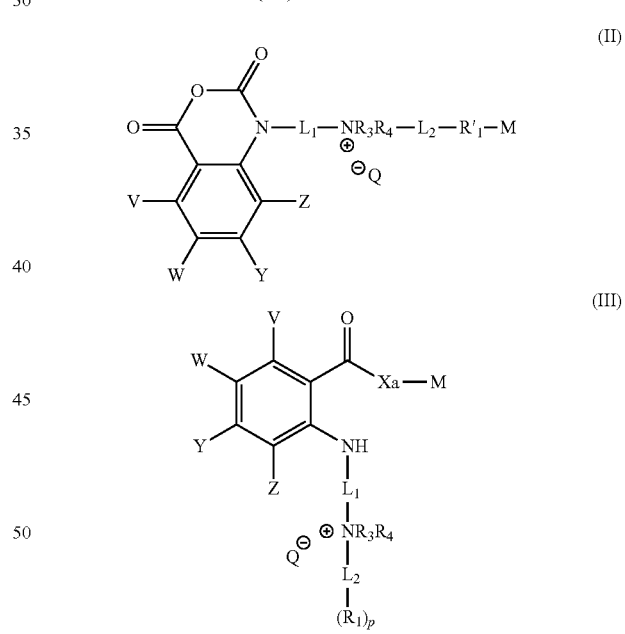

The variables V, W, Y, Z, L$_1$, L$_2$, Q$^-$, R$_3$, R$_4$, p and R$_1$ represent the same substituents as described for the derivatives of Formula (I) above including all of the various combinations and sub-combinations of each of the various variables. M represents a material and R'$_1$ represents a group formed from the reaction or interaction of and the material (M). For example, when R$_1$ is a chemically reactive group, M can have a complementary chemically reactive group and R'$_1$ represents the coupled product therefrom as shown in Table 8 below, for example. Alternatively, R'$_1$ can represent the interaction of a binding group of R$_1$ with the material. In some cases the anhydride function and the R$_1$ both can react with an amine. To differentiate the two potential sites of reaction the reactivity substituents on the aryl ring (V, W, Y, Z) can be varied to increase or decrease the reactivity of the anhydride.

The relative reactivity of the anhydride and $R_1$ of the isatoic derivative toward a. given material can be adjusted principally by the selection of an appropriate $R_1$ group. In addition, the groups on the aryl ring (V, W, Y, Z) and the groups for $R_3$, $R_4$ and the linker $L_2$ can be selected to affect the relative reactivity of the anhydride and $R_1$ of the isatoic derivative. For example, making V a bulky alkyl group would slow the rate of reaction at the anhydride moiety relative to $R_1$. Alternatively, making W, Y and Z electron withdrawing will increase the rate of reaction at the anhydride relative to $R_1$.

In addition to being able to tune the reaction rate of the anhydride portion of the molecule, the aromatic substituents (V, W, Y, Z) can include chemically reactive groups such as an azido or alkynyl, which would change an isatoic anhydride derivative of the present disclosure from a difunctional (anhydride and chemically reactive $R_1$), to a multi-functional reagent (anhydride, chemically reactive $R_1$ and one or more chemically reactive V, W, Y and/or Z). For example, isatoic anhydride derivative 57 below can react with an amine in a biological material via the anhydride to form an anthranilate having the dual functionality of a maleimide and an azide into the biomolecule.

57

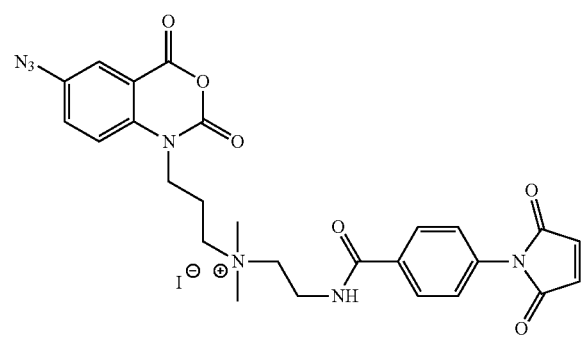

Such a multi-functional reagent thereby permits the option of connecting a biological material to two additional materials. In the case of the above example, the anthranilate can couple a material including a thiol to react with the maleimide and another material including an alkyne to react with the azide through a 1,3-dipolar azide/alkyne cycloaddition. This multi-valency is a valuable attribute to add to a material surface such as a biomolecule.

An aspect of the present disclosure includes modifying a material by combining an isatoic anhydride derivative with a material having a group that can chemically react with $R_1$ of the isatoic anhydride derivative. The relative reactivity of the anhydride and $R_1$ of the isatoic derivative toward a given material can be adjusted principally by the selection of an appropriate $R_1$ group. The groups on the aryl ring (V, W, Y, Z) and the groups for $R_3$, $R_4$ and the linker $L_2$ can be selected to affect the relative reactivity of the anhydride and $R_1$ of the isatoic derivative. In one embodiment of the present disclosure, the method includes combining an isatoic anhydride derivative having an NHS ester or a thioester as the chemically reactive $R_1$ group and a material having a primary amine to react with $R_1$ to give the derivative of Formula (II).

Another aspect of the present disclosure includes modifying a material by combining an isatoic anhydride derivative of the present disclosure with a material that can chemically react with the anhydride of the isatoic anhydride derivative, Scheme 3 illustrates an embodiment of combining an isatoic anhydride derivative of the present disclosure with a material.

Scheme 3

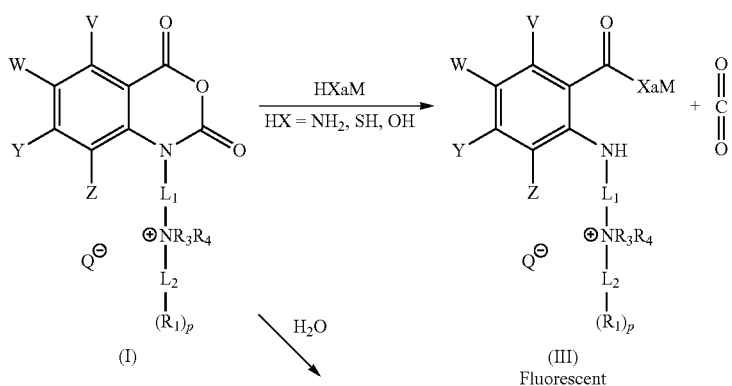

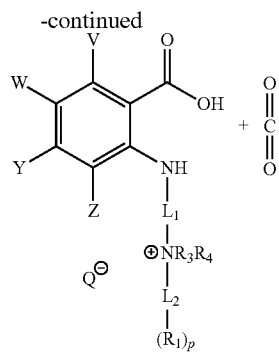

As shown in this Scheme 3, isatoic anhydride derivative of Formula (I) can be combined with a material (M) having a nucleophilic group HXa, wherein HXa represents a $NH_2$, $NHR_5$, SH, or OH group, for example, to form anthranilate having Formula (III) with the release of carbon dioxide. That is, isatoic anhydride derivative of Formula (I) can be conjugated with a material represented as HXaM to form Formula (III) where M is the material and Xa represents a NH, $NR_5$, S, or O group, for example. Advantageously, the anthranilate of Formula (III) is fluorescent. Hence, the coupling reaction illustrated in Scheme 3 can provide a real-time fluorescence signal indicating when the reaction is completed.

Further, the isatoic anhydride derivatives of the present disclosure can be advantageously water soluble, due to the quaternary ammonium group on the derivative, which permits modifying materials in aqueous media, e.g., water, which is a preferred media for most biological chemistry. Although water can react with the anhydride functionality of the isatoic derivative as shown in Scheme 3, it was discovered that the isatoic anhydrides of the present disclosure can react significantly faster with a material (M) than hydrolysis with water. Thus, an excess of the isatoic anhydride derivative can be used to form the anthranilate of Formula (III) in high yields and any unreacted isatoic anhydride derivative can be hydrolyzed thereafter and readily removed.

In addition, when $R_1$ is a chemically reactive group, the isatoic anhydride derivatives of the present disclosure can be made to react with a material (M) having a nucleophilic group at a significantly higher extent than any reaction with $R_1$. This can be done by the selection of $R_1$ and the groups for V, W, Y, Z as explained above.

For example, when V, W, Y, Z are all H and $R_1$ is an epoxide group, a material having a primary amine with react almost exclusively with the anhydride of the isatoic anhydride derivative. This was shown by rapid injection NMR experiments with derivative 1aa (described in the Example section below), when derivative 1aa (described in the Example section below) was reacted with 1 equivalent of n-butylamine (a model for the basic amine in a lysine residue of a protein) in $D_2O$ buffered to pH of 8.4 it was shown that the amine reacts with the anhydride function with no observable reaction with the epoxide group. However, when $R_1$ is an NHS ester as in derivative 1x (described in the Example section below), analysis showed that the reaction rates are similar for both the anhydride and the NHS ester toward n-butylamine. Thus, the substituents on the aryl ring (V, W, Y, Z) should be tuned to adjust the relative reaction rates. For example, making V a bulky alkyl group would slow the rate of reaction at the anhydride moiety relative to the NHS ester. Alternatively, making W or Y electron withdrawing will increase the rate of reaction at the anhydride relative to the NHS ester.

Materials that are useful for the present disclosure include, for example, a biological material (Bio) such as RNA and a functionalized derivative thereof, DNA and a functionalized derivative thereof, a protein, a peptide, a peptidomimetic, an enzyme, an aptamer, antibody, antibody fragment, a drug, sugar, starch, etc. As used herein a material is not limited to large molecules and can include small molecules such as drugs. Additional useful materials include polymers such as hydrolysable and biodegradable polymers, e.g., poly(lactic-co-glycolic acid) (PLGA), polycaprolactone (PCL)-polyethylene Glycol copolymers, and polymers that can be used for delivery of medicinal substances and as diagnostics. The materials useful for this disclosure further include a glass, ceramic, plastic, wood, textile, wool, paper, cellulose, metal, metal alloy, etc. The material can be in the size of a micro or nano-particle and in the shape of a flat sheet, a sphere, a rod. Nanoparticles include organic, inorganic or an inorganic/organic polymer hybrid. Other materials that can be used in the present disclosure include form factors such as a 16 or 96 well plate, for example. Additional materials that are useful in the present disclosure include those that have functionalities such as wherein the material can be represented as $HXaL_3-R''_1$.

Another aspect of the present disclosure includes anthranilates of Formula (III) in which the material is a biological material. Such anthranilate derivatives can be represented according to Formula (IIIA):

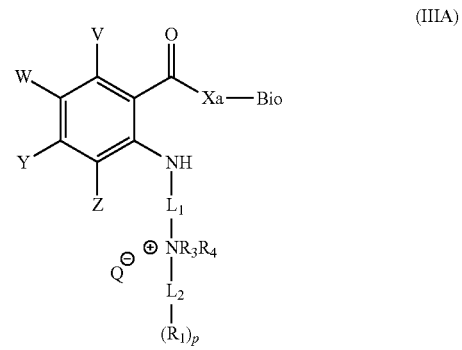

The variables V, W, Y, Z, $L_1$, $L_2$, $Q^-$, $R_3$, $R_4$, p, $R_1$, and Xa, represent the same substituents as described above including all of the various combinations and sub-combinations of each of the various variables and the group "Bio" represents a biological material.

In one embodiment of the present disclosure, an anthranilate of Formula (IIIA) includes a biological material, such as RNA, an RNA aptamer, and a functionalized derivative thereof (e.g. Olaptesed pegol (NOX-A12) and Emapticap pegol (NOX-E36), *Noxxon Pharma*), DNA, a DNA aptamer, and a functionalized derivative thereof (e.g. anti-nucleolin aptamer AS1411), a protein (e.g., Streptavidin, Neutravidin, Avidin), a peptide (e.g., Arginine-Glycine-Aspartic Acid (RGD), cyclic-RGD etc.), a peptidomimetic (e.g., $\alpha_v\beta_3$ antagonist S247 etc.), an enzyme (e.g., Elspar (asparaginase)), a peptide aptamer, an antibody (Ab) (e.g., Herceptin® (Trastuzumab), Avastin® (bevacizumab), ERBITUX® (cetuximab) etc.), antibody fragment (e.g., antigen binding fragments (Fab) e.g. LUCENTIS® (ranibizumab), single chain variable fragments (scFv) and third generation 3G molecules), a sugar (Glucose, Glucosamine etc.), a starch, etc.

For example, isatoic anhydride derivatives can be used to modify a biological material such as RNA and a functionalized derivative thereof, DNA and a functionalized derivative thereof, a protein, a peptide, a peptidomimetic, an enzyme, an aptamer, antibody, antibody fragment, a drug, sugar, starch, etc., by coupling a biotin group to the material. That is, when an isatoic anhydride derivative of the present disclosure includes a biotin group (e.g., $R_1$ of Formula (I) is a biotin group), such derivatives can be used in the biotinylation of a biological material. Biotinylation of biological materials can be carried out, for example, by combining an isatoic anhydride derivative of the present disclosure which includes a biotin group with a biological material. Such a combination forms an anthranilate derivative such as shown in Formula (IIIA) wherein Bio is a biological material and $R_1$ is a biotin group. Additional examples of anthranilates are provided below.

Labeling and Conjugating an Antibody (Ab) with Biotin

Isatoic anhydride derivatives of the present disclosure including a biotin group are particularly advantageous in biotinylation reactions because the degree of biotinylation can be reasonably quantified. The biotinylation of various biological materials involves the covalent attachment of at least one molecule of biotin to the material. Biotin forms a highly specific non-covalent complex with streptavidin (and other streptavidin analogues such as avidin or neutravidin) which can be exploited to isolate, purify, and identify, the resulting biotinylated molecule. Knowing the degree of biotinylation, i.e., the amount of biotin added to a material, is highly desirable (so as not to interfere with the bioactivity of the molecule being derivatized). As such it highly desirable that the resulting degree of biotinylation be quantifiable. Because biotin possesses no inherently useful chromophore, this quantification is typically achieved through the use of fluorescently labeled streptavidin (or avidin and neutravidin), or by secondary assays such as anti-biotin antibodies or enzymatic activity assays using avidin/streptavidin linked horseradish peroxidase or alkaline phosphatase.

However, isatoic anhydride derivatives of the present disclosure including a biotin group can ameliorate these detection issues and be used in the construction of biotinylated biomolecules. In one such example and as illustrated in Scheme 4 below, an antibody (i.e., anti-MUC1 antibody BC2 (abcam, ab89492)) can be labeled with an isatoic anhydride derivative including a biotin group such as derivative 1s to afford a BC2-1s bioconjugate.

Scheme 4

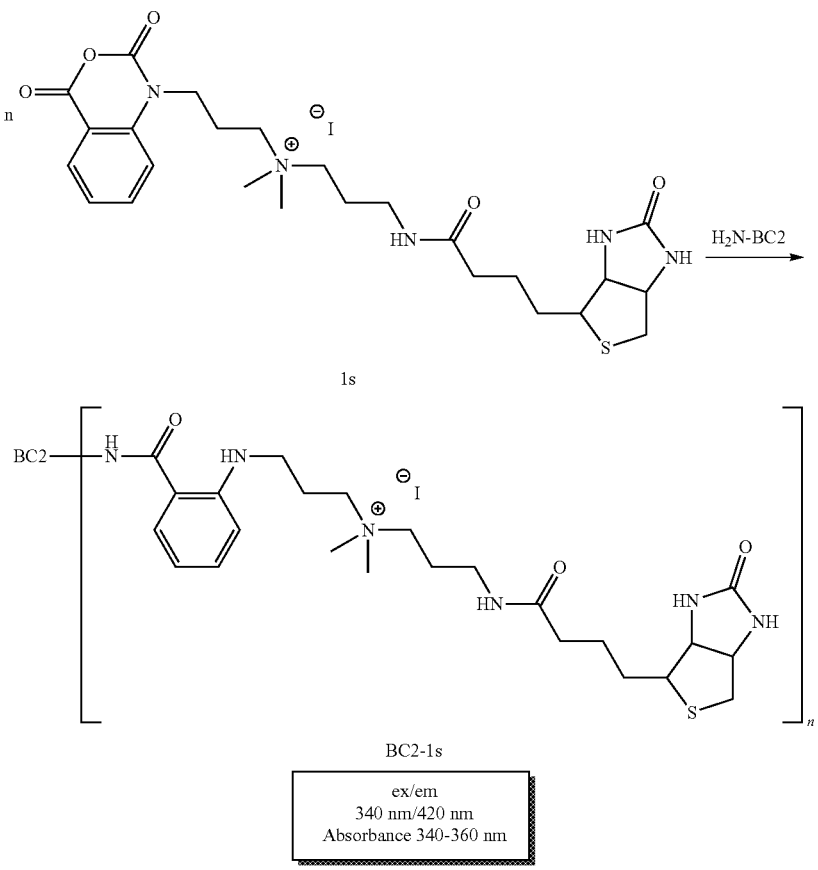

The unique absorbance (340-360 nm) inherent in the anthranilate (i.e., the conjugate of the isatoic anhydride derivative and the biological material) can be used to quantify the degree of biotinylation directly without the need of secondary assay detection. Additionally, the labeled BC2-1s bioconjugate will possess a unique fluorescence spectrum (excitation/emission 340 nm/420 nm) due to the anthranilate moiety which can be used to readily identify the biotinylated BC2-1s bioconjugate under a variety of conditions where fluorescence detections is convenient (e.g., in-gel fluorescence, etc.)

Labeling and Conjugating an Antibody (Ab) with a Fluorophore

Another application of the isatoic anhydride derivatives of the present disclosure includes modifying biological materials by coupling fluorescent compounds thereto. The fluorescent labeling of antibodies is a widespread practice for a variety of applications in the biological and biomedical fields alike. Examples of this include the use of fluorescently labeled antibodies for the detection of highly specific antigens in which the presence thereof is diagnostic of a particular physiological state.

Isatoic anhydride derivatives of the present disclosure including a chemically reactive group (e.g., $R_1$ of Formula (I) is a chemically reactive group) can be used to couple a biological material, e.g., an antibody, with a fluorophore. In one such example and as illustrated in Scheme 5 below, the anti-EGFR antibody ICR10 (abcam, ab231) can be labeled with an isatoic anhydride derivative including a chemically reactive group such as derivative 1w to afford an ICR10-1w bioconjugate.

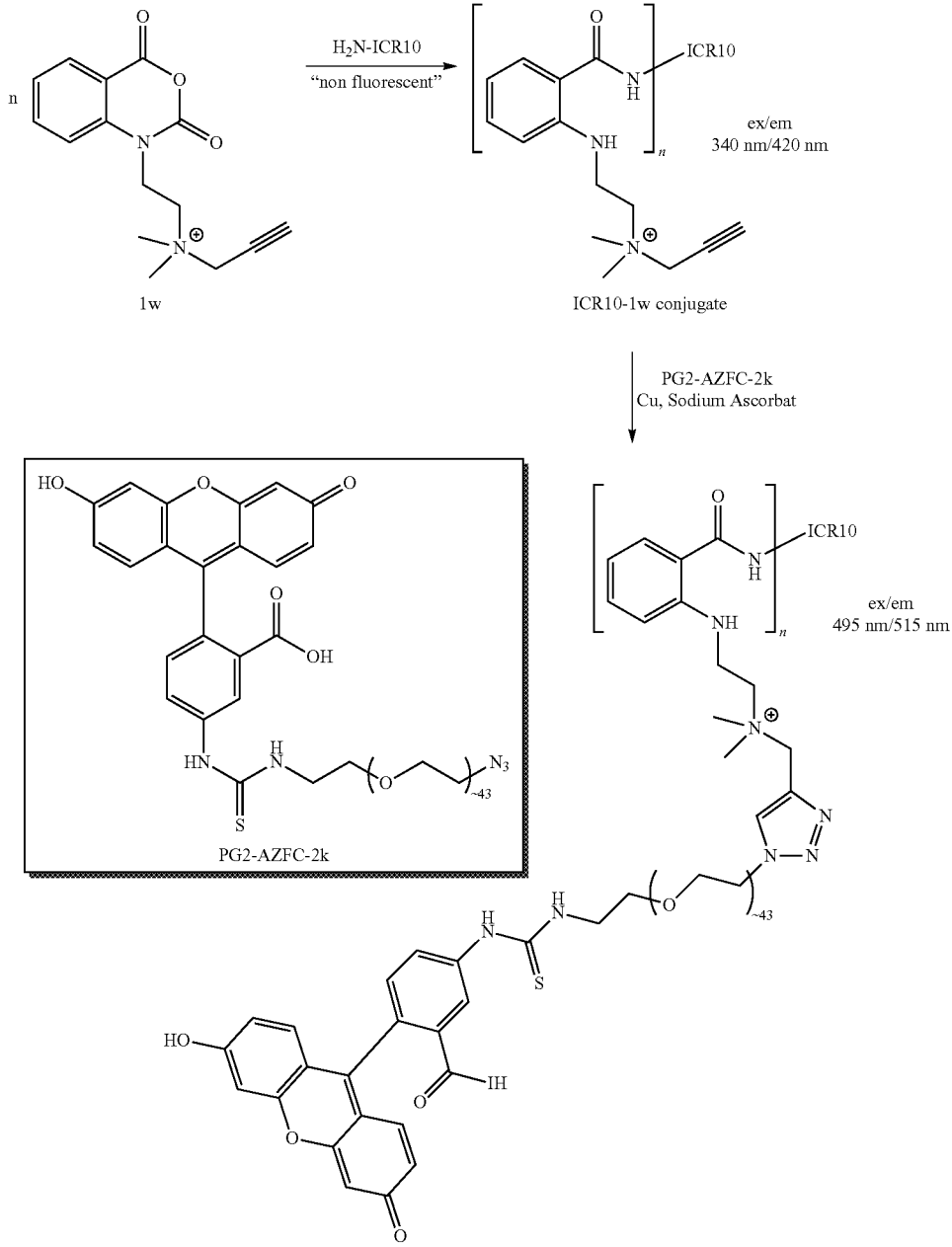

Scheme 5

Derivatization of ICR10 with 1w will impart a unique absorption profile (340-360 nm) and will further render ICR10 fluorescent with excitation/emission maxima of 340 nm/420 nm respectively. These properties will enable the end user to readily determine the degree of functionalization of the ICR10 Ab upon derivatization with 1w. Further, the alkyne chemically reactive group installed on the antibody upon treatment with 1w allows coupling another material, i.e., a fluorophore, onto the ICR10-1w conjugate. Coupling the ICR10-1w conjugate with FITC-PEG-N$_3$ (NANOCS, PG2-AZFC-2k) through the chemically reactive alkyne group yields an ICR10 antibody labeled with fluorescein. This conjugate will now exhibit excitation emission wavelengths of around 495 nm/515 nm (indicative of fluorescein) making this conjugate suitable for applications where fluorescent detection is desirable (e.g., confocal microscopy, flow assisted cell sorting (FACS), etc.).

Labeling and Conjugating an Antibody (Ab) with a Drug

Another application of the isatoic anhydride derivatives of the present disclosure includes modifying biological materials by coupling drugs thereto. Antibody-drug conjugates (ADCs) are a relatively new class of targeted therapeutics with applications primarily in cancer chemotherapies. One common strategy for the construction of ADCs is the installation of the drug through a Michael Addition reaction between a thiol native to the antibody (or antibody fragment) and a maleamide modified drug.

Isatoic anhydride derivatives of the present disclosure including a chemically reactive group (e.g., R$_1$ of Formula (I) is a chemically reactive group) can be used to couple a biological material, e.g., an antibody, with a drug. In one such example and as illustrated in Schemes 6A and 6B below, an antibody can be conjugated with a drug.

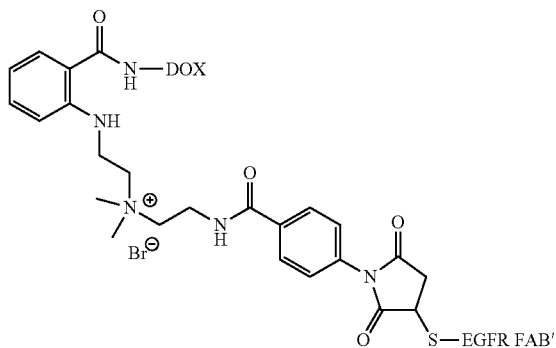

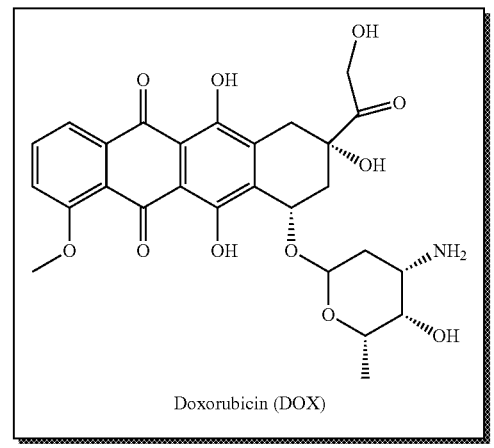

Doxorubicin (DOX)

Scheme 6A

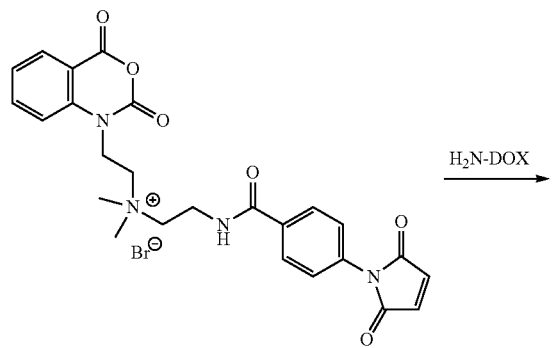

Scheme 6B

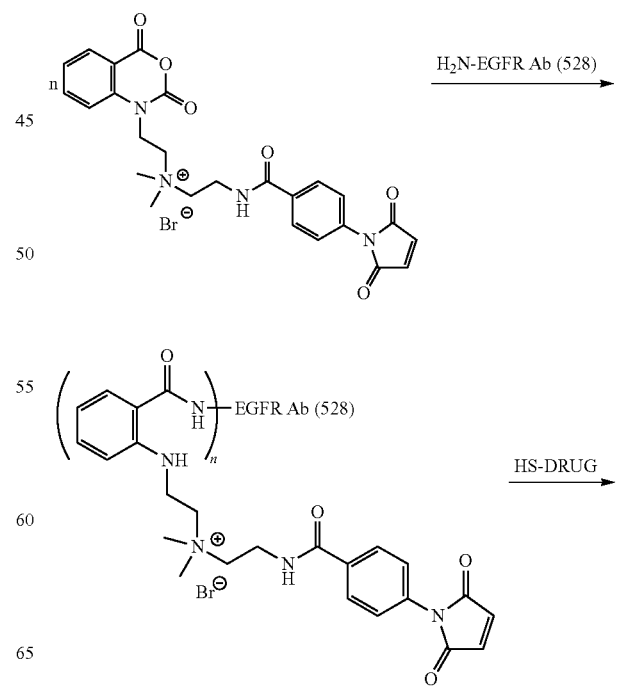

-continued

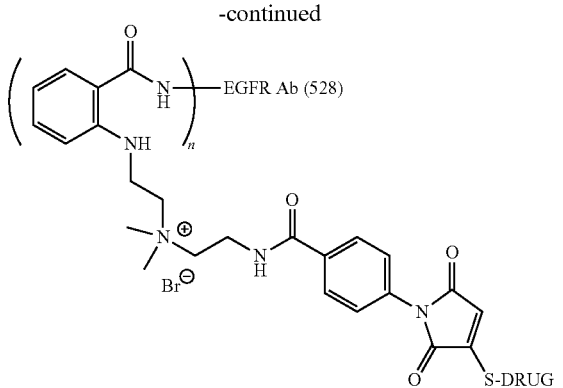

For example, the antibody fragment of the EGFR Antibody (528) (Santa Cruz, sc-120) can be chemoselectively labeled with a doxorubicin-2r conjugate (Scheme 6A). This strategy can be used for a variety of drugs with a nucleophilic center capable of undergoing modification with 2r. Alternatively and as shown in Scheme 6B, ADCs of the EGFR Antibody (528) can be generated using 2r by incorporating the maleamide onto the Ab through modification of lysine residues native to the Ab. Using the unique absorbance of the Ab-2r conjugate (absorbance 340-360 nm) the number of maleamide residues incorporated onto the Ab can be determined. Further a drug of interest bearing an appropriately reactive thiol can be chemoselectively incorporated to the Ab-2r via Michael Addition between the thiol drug and maleamide functionalities.

Sulfo-NHS and NHS based Chemistry

Another application of the isatoic anhydride derivatives of the present disclosure includes using such derivatives as a replacement for sulfo-NHS (N-hydroxysulfosuccinimide) and NHS (N-hydroxysuccinimide) based chemistry for modifying materials. The quaternary ammonium group on the isatoic, anhydride derivatives of the present disclosure promotes water solubility of the derivative which is advantageous in biological chemistry that uses aqueous reaction media. The isatoic anhydride derivatives of the present disclosure also offer the advantage that the extent of the reaction can be reasonably quantified since the isatoic anhydride has a distinct fluorescent and UV signature. Isatoic anhydride derivatives of the present disclosure including a sulfo-NHS or NHS group (e.g., $R_1$ of Formula (I) is a (sulfo)N-hydroxysuccinimide ester group or an N-hydroxysuccinimide ester) can be used as a replacement for sulfo-NHS and NHS based chemistry for modifying materials.

Functionalization and Immobilization of Materials

Another application of the isatoic anhydride derivatives of the present disclosure includes modifying materials such as glass. The functionalization of glass surfaces is widely practiced for applications within the biotechnology industry. For example, glass surfaces bearing epoxide functionalities are widely used for the immobilization of a variety of biological materials such as proteins, peptides, and modified and unmodified oligonucleotides.

Isatoic anhydride derivatives of the present disclosure including a chemically reactive group (e.g., $R_1$ of Formula (I) is an epoxide reactive group) can be used to functionalize a material, e.g., glass. The functionalized material can then be used to immobilize a biological material. For example and as shown in FIG. 1, an isatoic anhydride derivatives of the present disclosure including an epoxide such as derivative 1aa can be used in the preparation of epoxide coated glass surfaces. The manufacture of epoxide coated glass surfaces with 1aa can be readily achieved by a simple two-step process. First, glass surfaces can be treated with (3-aminopropyl)triethoxysilane (APTES) (Sigma-Aldrich, A3648) to provide a nucleophilic surface. Secondly, a solution of 1aa can be applied to the surface wherein the 1aa would react with the amine of the APTES almost exclusively at the anhydride of 1aa leaving an epoxide surface for derivatization in aforementioned applications.

Coupling biological materials to a radio label through isatoic anhydride derivative Isatoic anhydride derivatives of the present disclosure including a boron or silicon functionality are useful in the construction of materials where the incorporation of the fluorine-18 ($^{18}$F) radionucleide is desired. The $^{18}$F radionucleide is commonly used in positron emission tomography (PET). The application of PET as nuclear medical imaging technique is widespread within the medical community. PET utilizes positron-emitting radionuclides for detection of gamma rays. Typically this is achieved through introduction of metabolically active small molecules containing a radionuclide of choice. Currently the industry standard radiopharmaceutical utilized for PET is 2-deoxy-2-($^{18}$F)fluoro-D-glucose (FDG). Operationally, this process requires the systemic administration of FDG, which is then indiscriminately metabolized by metabolically active cells. Accordingly, uptake is a function of metabolic activity. Owing to the increased metabolic activity of cancerous cells, PET is commonly utilized as a means of illuminating cancer and cancer metastasis. Although there is an increased uptake by cancer cells relative to healthy cells, it is highly desirable to limit the potentially harmful radioactive exposure specifically to sites of disease. The use of nanoparticles adorned with cellular targeting agents (e.g., aptamers, antibodies, antibody fragments, peptides, peptidomimetics, sugars etc.) for use as molecular scaffolds as selective delivery agents of $^{18}$F labeled imaging agents can effectively ameliorate the problems associated with the systemic delivery of small molecules incorporating $^{18}$F.

Figure 2:
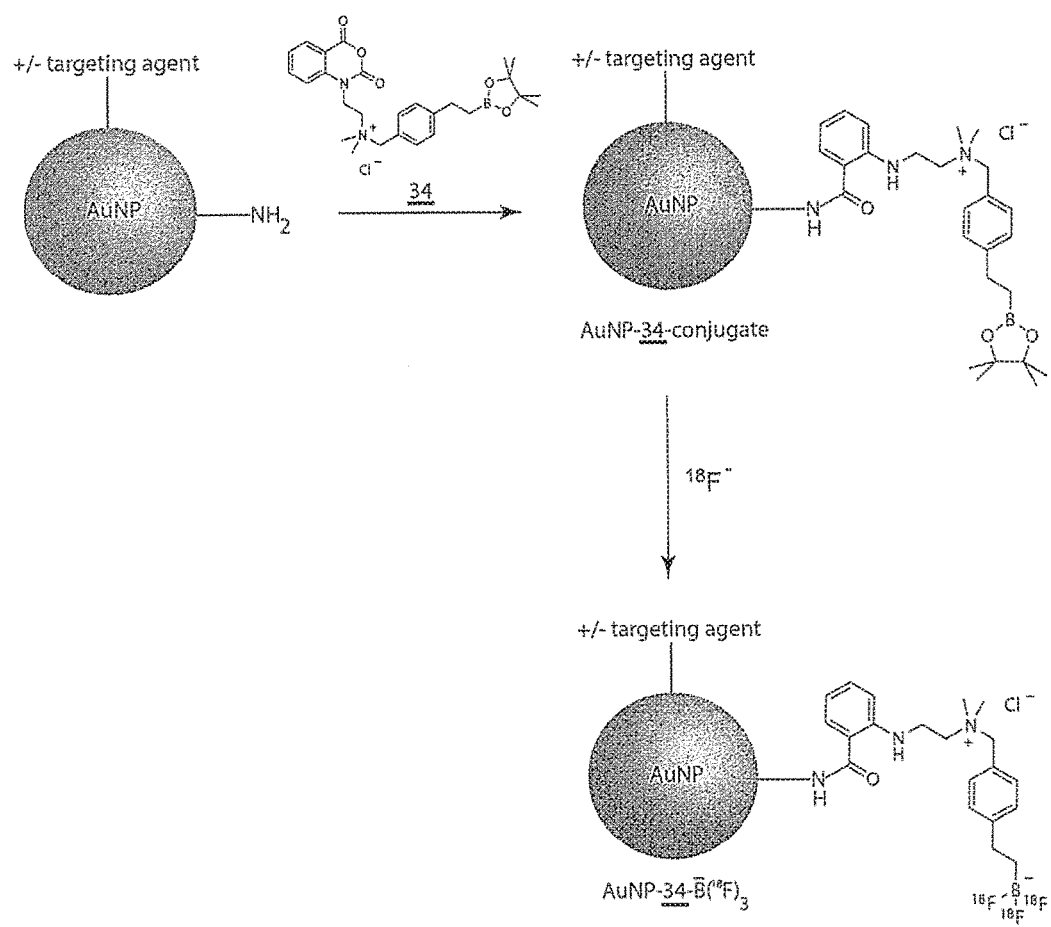
FIG. 2 illustrates coupling biological materials to a radio label through an isatoic anhydride derivative of the present disclosure.

In one such example and as illustrated in FIG. 2, a nanoparticle having an amine functional group, e.g., a 50 nm gold (Au) nanoparticle (NP) with an amine functionalized surface (available from Sigma Aldrich), can be labeled with an isatoic anhydride derivative including a boronate ester group such as derivative 34 to afford an AuNP-34 conjugate. This derivative can then be treated directly with an $^{18}$F$^-$ source to prepare AuNP-34-B($^{18}$F)$_3^-$ derivatives suitable for in vivo imaging and diagnostics.

In another example, an amine functionalized nanoparticle can be labeled with an isatoic anhydride derivative including a siloxane group such as derivative 43 to afford a nanoparticle-43 conjugate. This derivative can then be treated directly with an $^{18}$F$^-$ source to prepare NP-43-Si($^{18}$F)$_3^-$ derivatives suitable for in vivo imaging and diagnostics.

Anthranilate with Multiple Functionalities

Another aspect of the present disclosure includes anthranilates having multiple functionalities. Such anthranilates have the structure of Formula (IIIB) shown in the various schemes below.

For example, Scheme 7A illustrates an embodiment of combining an isatoic anhydride derivative of the present disclosure with a material, wherein the material can be represented as HXaL$_3$-R"$_1$, to generate an anthranilate having multiple functionalities.

Scheme 7A

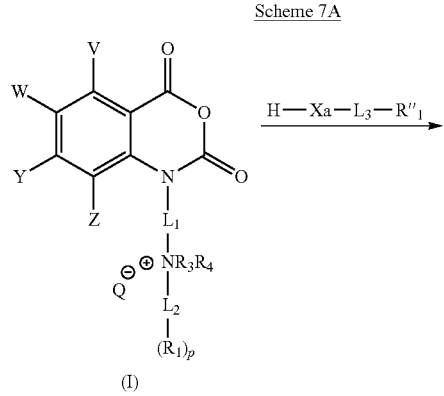

(I)

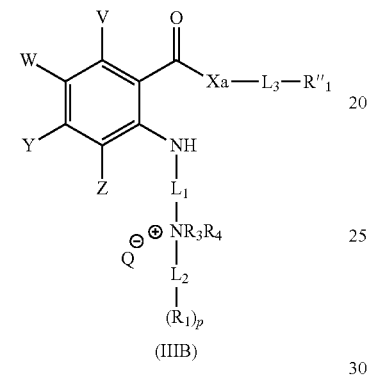

(IIIB)

The variables V, W, Y, Z, $L_1$, $L_2$, $Q^-$, $R_3$, $R_4$, p and $R_1$ represent the same substituents as described for the derivatives of Formula (I) above including all of the various combinations and sub-combinations of each of the various variables. HXa represents a $NH_2$, $NHR_5$, SH, or OH group, for example, and $L_3$ and $R''_1$ represent, respectively, the same groups as described for $L_1$ and $R_1$ of Formula (I) above including all of the various combinations and sub-combinations of each of the various variables.

Anthranilates of Formula IIIB can be prepared by simply adding a material represented as HXa-$L_3$ $R''_1$ to an isatoic anhydride derivative of Formula (I). When HXa-$L_3$ $R''_1$ is an amine the reaction can be conveniently carried out in water or water and a miscible organic solvent such as acetonitrile if needed to aid in the dissolution of HXa-$L_3$ $R''_1$. When HXa-$L_3$ $R''_1$ is an alcohol an anhydrous polar aprotic solvents such as DMSO and DMF can be used to solubilize I for the reaction.

Alternatively, the anthranilates of Formula (IIIB) can be prepared by the routes shown in Schemes 7B and 7C below.

Scheme 7B

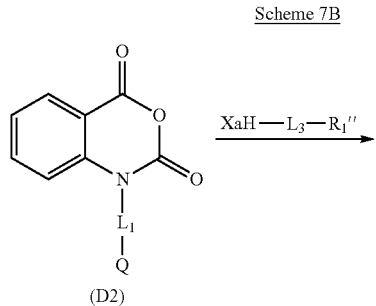

(D2)

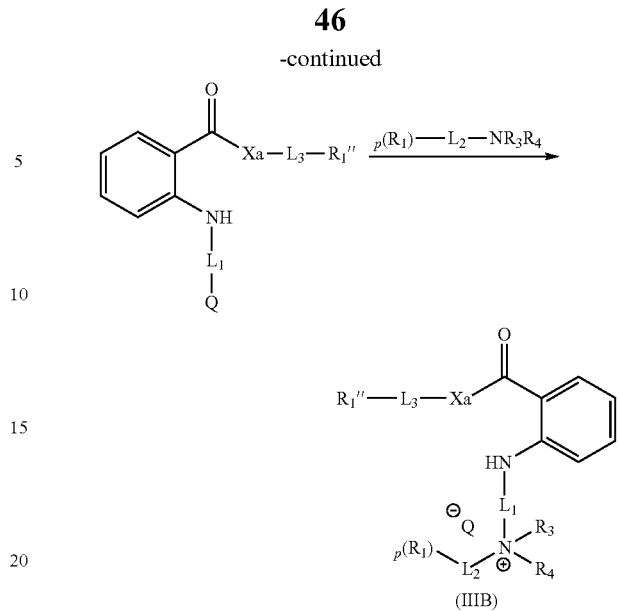

Scheme 7C

In these alternate routes the last step would be carried out in acetone having the advantage of the self-cleaning quaternization step being last.

In an embodiment of the present disclosure, anthranilates of Formulae (IIIB) can include the groups provided in Table 6 below.

TABLE 6
Examples of anthranilates of Formula (IIIB)
| —$L_1QNR_3R_4L_2(R_1)p$ | —Xa—$L_3R''_1$ |
|---|---|
| 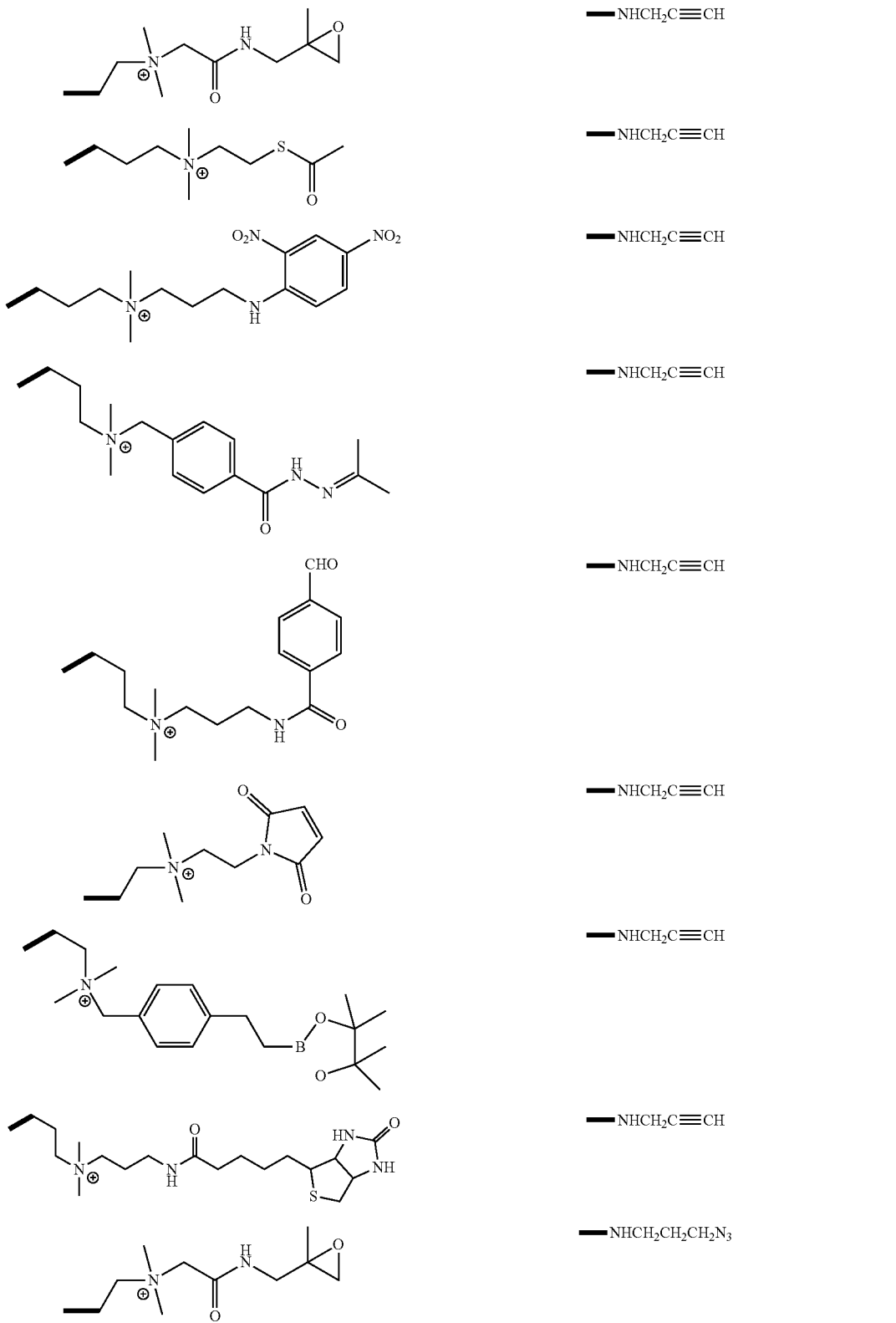 | —$NHCH_2C\equiv CH$ |
| | —$NHCH_2C\equiv CH$ |
| | —$NHCH_2C\equiv CH$ |
| | —$NHCH_2C\equiv CH$ |
| | —$NHCH_2C\equiv CH$ |
| | —$NHCH_2C\equiv CH$ |
| | —$NHCH_2C\equiv CH$ |
| | —$NHCH_2C\equiv CH$ |
| | —$NHCH_2CH_2CH_2N_3$ |

TABLE 6-continued

Examples of anthranilates of Formula (IIIB)

| —L$_1$QNR$_3$R$_4$L$_2$(R$_1$)$p$ | —Xa—L$_3$R″$_1$ |
|---|---|
| (structure) | —NHCH$_2$CH$_2$CH$_2$N$_3$ |
| (structure) | —NHCH$_2$CH$_2$CH$_2$N$_3$ |
| (structure) | —NHCH$_2$CH$_2$CH$_2$N$_3$ |
| (structure) | —NHCH$_2$CH$_2$CH$_2$N$_3$ |
| (structure) | —NHCH$_2$CH$_2$CH$_2$N$_3$ |
| (structure) | —NHCH$_2$CH$_2$CH$_2$N$_3$ |
| (structure) | —NHCH$_2$CH$_2$CH$_2$N$_3$ |
| (structure) | (structure) |

TABLE 6-continued
Examples of anthranilates of Formula (IIIB)
| —L₁QNR₃R₄L₂(R₁)p | —Xa—L₃R″₁ |
|---|---|
| 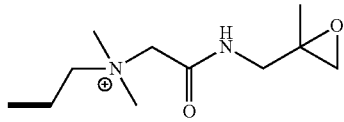 | 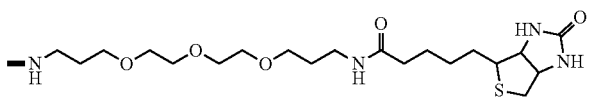 |
| 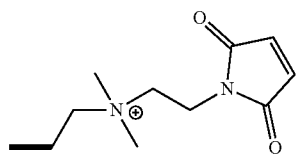 | 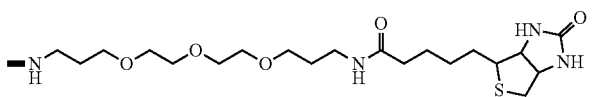 |
| 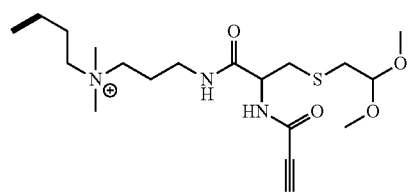 | —NHCH₂CH₂CH₂Si(OMe)₃ |
| 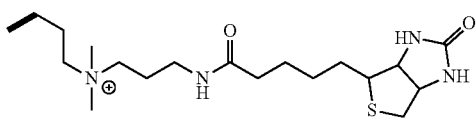 | —NHCH₂CH₂CH₂Si(OMe)₃ |
| 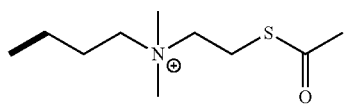 | —NHCH₂CH₂CH₂Si(OMe)₃ |
| 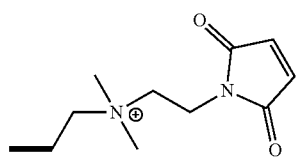 | —NHCH₂CH₂CH₂Si(OMe)₃ |
| 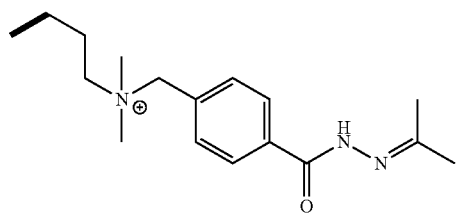 | |
| 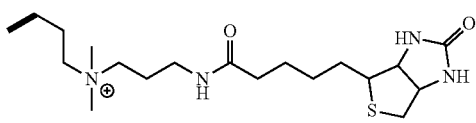 | 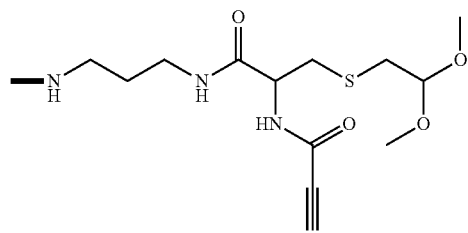 |

TABLE 6-continued

Examples of anthranilates of Formula (IIIB)

| ━L$_1$QNR$_3$R$_4$L$_2$(R$_1$)$p$ | ━Xa━L$_3$R″$_1$ |
|---|---|
| 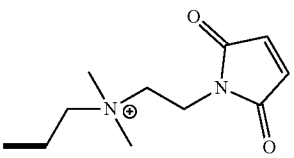 | 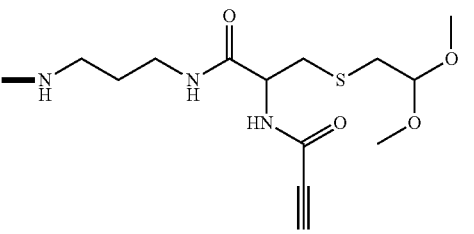 |
| 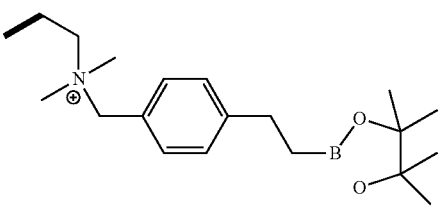 | 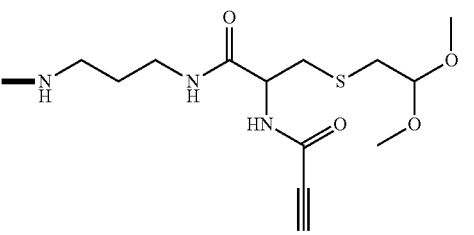 |
| 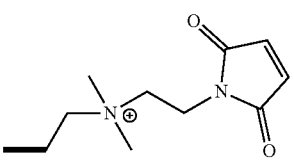 | ━NHCH$_2$CH$_2$NH━C(=O)━O(CH$_2$CH$_2$O)$_n$CH$_3$ |
| ━CH$_2$CH$_2$N$^+$(Me)$_2$CH$_2$CH$_2$CH$_2$N$_3$ | ━NHCH$_2$CH$_2$NH━C(=O)━O(CH$_2$CH$_2$O)$_n$CH$_3$ |
| 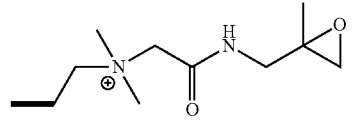 | ━NHCH$_2$CH$_2$NH━C(=O)━O(CH$_2$CH$_2$O)$_n$CH$_3$ |
| 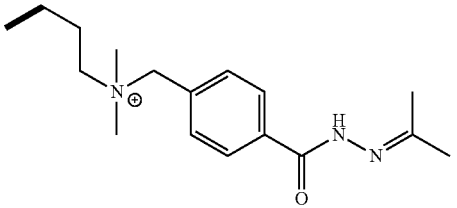 | ━NHCH$_2$CH$_2$NH━C(=O)━O(CH$_2$CH$_2$O)$_n$CH$_3$ |
| 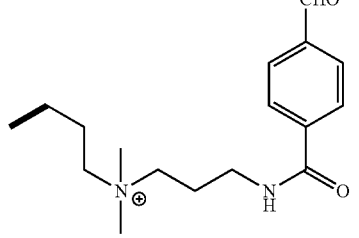 | ━NHCH$_2$CH$_2$NH━C(=O)━O(CH$_2$CH$_2$O)$_n$CH$_3$ |
| 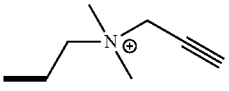 | ━NHCH$_2$CH$_2$NH━C(=O)━O(CH$_2$CH$_2$O)$_n$CH$_3$ |

TABLE 6-continued
Examples of anthranilates of Formula (IIIB)
| —L₁QNR₃R₄L₂(R₁)p | —Xa—L₃R″₁ |
|---|---|
| 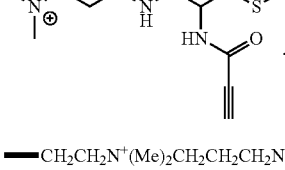 |  |
| —CH₂CH₂N⁺(Me)₂CH₂CH₂CH₂N₃ | —O(CH₂CH₂O)ₙCH₃ |
| 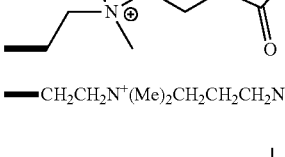 | —O(CH₂CH₂O)ₙCH₃ |
| —CH₂CH₂N⁺(Me)₂CH₂CH₂CH₂N₃ | —O(CH₂CH₂O)ₙCH₃ |
| 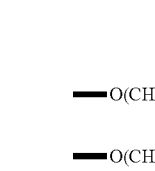 | —O(CH₂CH₂O)ₙCH₃ |
| 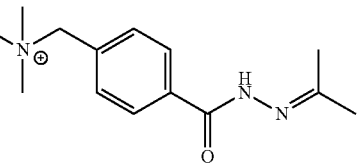 | —O(CH₂CH₂O)ₙCH₃ |
|  | —O(CH₂CH₂O)ₙCH₃ |
| 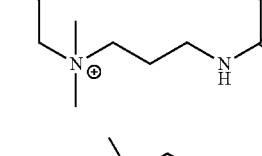 |  |

TABLE 6-continued

Examples of anthranilates of Formula (IIIB)

| —L$_1$QNR$_3$R$_4$L$_2$(R$_1$)p | —Xa—L$_3$R″$_1$ |
|---|---|
| —CH$_2$CH$_2$N$^+$(Me)$_2$CH$_2$CH$_2$CH$_2$N$_3$ | 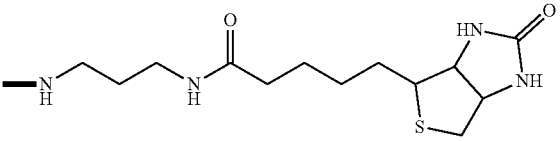 |
| 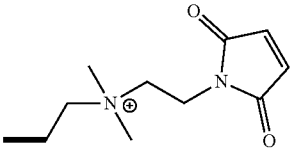 | 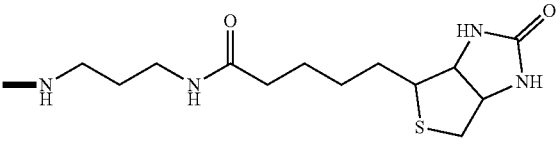 |
| —CH$_2$CH$_2$N$^+$(Me)$_2$CH$_2$CH$_2$CH$_2$N$_3$ | 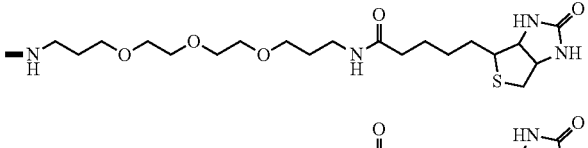 |
| 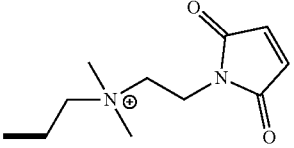 | 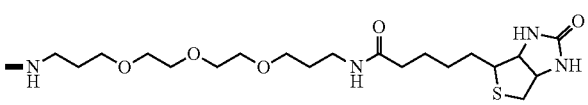 |
| 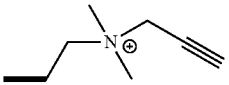 | 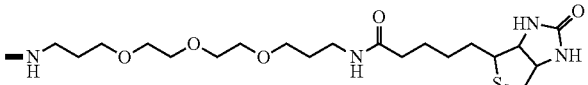 |

In another embodiment of the present disclosure, anthranilates of Formulae (IIIA) can include the groups provided in Table 7 below.

TABLE 7

Examples of anthranilates of Formula (IIIA)

| —L$_1$QNR$_3$R$_4$L$_2$(R$_1$)p | —Xa-Bio |
|---|---|
| All of the same groups provided in Table 6 | —NH-Ab, —NH-Ab fragment, —NH-Aptamer, —NH-Protein, —NH-Enzyme, —NH-peptide, —NH-peptidomimetic, —NH-Sugar, —O-Sugar, —O-Starch |

Coupling Materials Through Complementary Isatoic Anhydride Derivatives

Figure 3:
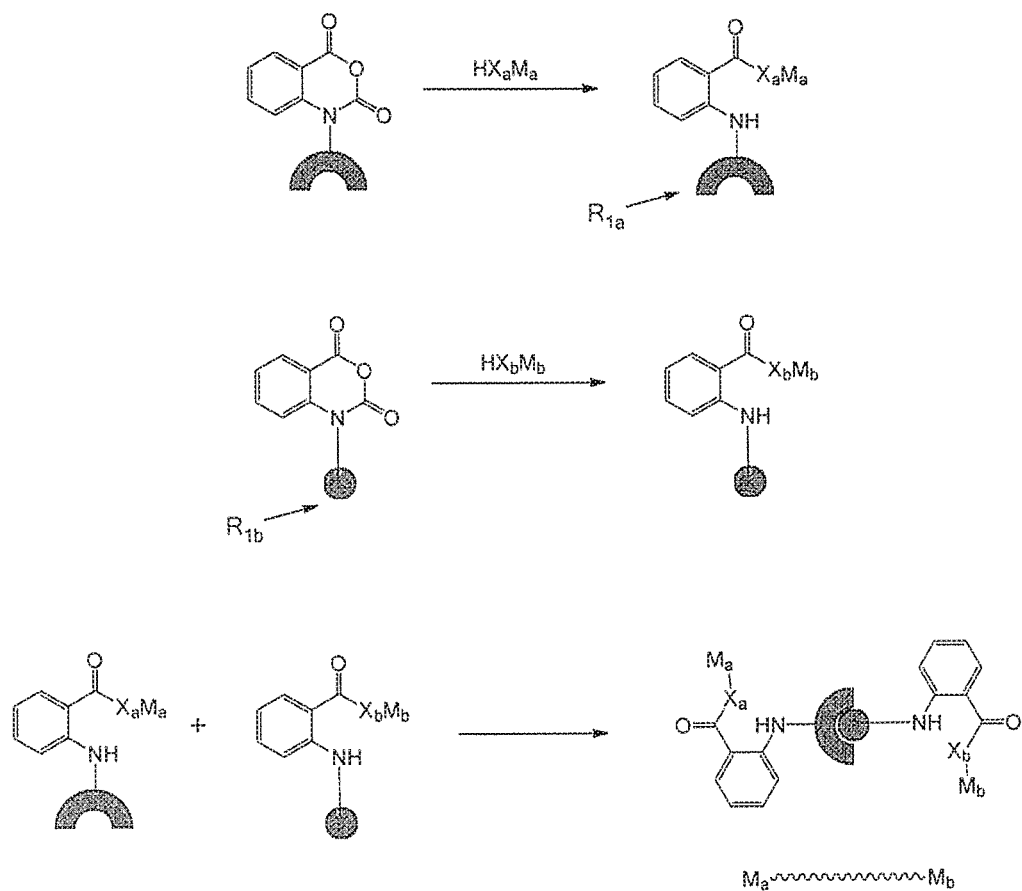
FIG. 3 illustrates a two-step a coupling reaction in which isatoic anhydride derivatives of the present disclosure are used to couple two materials to one another.

Additional applications of the isatoic anhydride derivatives of the present disclosure include coupling different materials through complementary isatoic anhydride derivatives. For example, FIG. 3 illustrates a general two-step coupling reaction in which isatoic anhydride derivatives of the present disclosure are used to couple two materials (HX$_a$M$_a$ and HX$_b$M$_b$) to one another using complementary R$_1$ chemically reactive groups, e.g. R$_{1a}$ and R$_{1b}$ on two different derivatives. The complementary reactive groups, R$_{1a}$ and R$_{1b}$, each independently represent chemically reactive groups that can react with each other. The R$_{1a}$ and R$_{1b}$ groups are illustrated in FIG. 3 as a semicircle and a circle, respectively. The R$_{1a}$ and R$_{1b}$ groups can be selected among groups that readily form covalent chemical bonds such as is known in click chemistry reactions.

As shown in the figure, a first isatoic anhydride derivative having an N-substituent which includes a quaternary ammonium group and group (R$_{1a}$) is combined with material HX$_a$M$_a$. and a second isatoic anhydride derivative having an N-substituent which includes a quaternary ammonium group and a second group (R$_{1b}$) is combined with material HX$_b$M$_b$. As further illustrated in FIG. 3, the first group (R$_{1a}$) can chemically react or bind with the second group (R$_{1b}$) to couple the two materials.

In an embodiment of the present disclosure, different materials are coupled through the use of a first and second isatoic anhydride derivative. The first isatoic anhydride derivative can have the structure of Formula (IVA) and the second isatoic anhydride derivative has the structure of Formula (IVB) as follows:

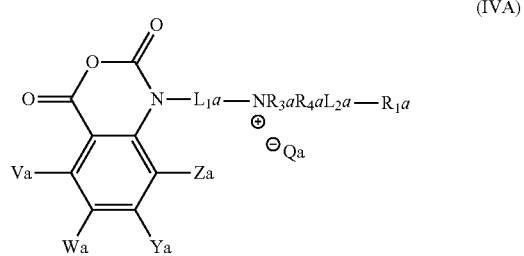

-continued

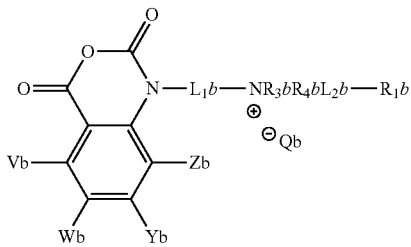

(IVB)

wherein Va, Vb, Wa, Wb, Ya, Yb, Za, Zb, $L_1a$, $L_2a$, $L_1b$, $L_2b$, $Q^-a$, $Q^-b$, $R_3a$, $R_3b$, $R_4a$, $R_4b$ independently represent groups from V, W, Y, Z, $L_1$, $L_2$, $Q^-$, $R_3$, $R_4$, described above for Formula I, respectively, including all of the various combinations and sub-combinations of each of the various variables. The groups $R_{1a}$ and $R_{1b}$ represent complementary chemically reactive groups as selected from $R_1$.

For example, the $R_{1a}$ and $R_{1b}$ groups can be selected among groups that readily form covalent chemical bonds such as is known in click chemistry reactions, e.g., $R_{1a}$ and $R_{1b}$ can be selected among an azide, alkyne, maleimide, protected thiol, alkene, hydrazone, aldehyde, ketone, acetal and ketal. Table 8 below illustrates complementary reactive groups for $R_{1a}$ and $R_{1b}$.

TABLE 8

| $R_{1a}$ | $R_{1b}$ | Coupling product from $R_{1a}$ + $R_{1b}$ |
|---|---|---|
| alkene (C=C) arylalkenyl (Ph—C=C) | thiol (—S—H), a disulfide (a thiol precursor) such as 2-pyridinyl disulfide (—S—S-pyridinyl), a thioester (a thiol precursor) | Thioether |
| azide ($N_3$) | alkyne (C≡C) | A triazole |
| hydrazone (N—N=$CME_2$) a hydrazide precursor | acetal $(C(OR)_2$ an aldehyde precursor or an aldehyde or ketone | A hydrazone |
| maleimide (Cyclic $N(CO)_2C=C$) | thiol (—S—H), a disulfide (a thiol precursor) such as 2-pyridinyl disulfide (—S—S-pyridinyl), a thioester (a thiol precursor) | A thioether |
| epoxide | amine | β-amino alcohol |

Coupling reactions of the isatoic anhydride derivative of the present disclosure can include, for example, when $R_{1a}$ is an alkene and $R_{1b}$ is a thiol. The $R_{1a}$ and $R_{1b}$ groups can be coupled using light, through the formation of a carbon-sulfur bond. In other instances, an azide-containing or alkyne-containing moiety of a compound described herein can be used to couple the compound to another chemical species through the formation by click chemistry of a carbon-nitrogen heterocycle from the azide or alkyne functional group and an alkyne or azide functional group of the other chemical species.

Kits

In another aspect of the present disclosure, isatoic anhydride derivative having an N-substituent which includes a quaternary ammonium group can be included in a kit. Such kits can be prepared and sold to connect biomolecules together or to connect biomolecules to other materials for delivering pharmaceuticals or to connect biological materials to a detectable label such a as a radio label or fluorophore or both.

A kit comprising at least a first isatoic anhydride derivative having an N-substituent which includes a quaternary ammonium group. The kit can further comprise a second isatoic anhydride derivative having an N-substituent which includes a quaternary ammonium group, wherein the first isatoic anhydride derivative includes a first chemically reactive group, and the second isatoic anhydride derivative includes a second chemically reactive group that can chemically react with the first chemically reactive group of the first isatoic anhydride derivative to couple the first and second isatoic anhydride derivatives. In an embodiment of the present disclosure, the first isatoic anhydride derivative can have the structure of Formula (IVA) and the second isatoic anhydride derivative has the structure of Formula (IVB). In an embodiment of the present disclosure, a kit includes one or more compounds of Formulae 4, 5, 7, or 8 in Table 1, e.g. an azide and alkyne from Formula 5 or a hydrazide and aldehyde from Formula 7.

The kit can also include instructions on how to use the first and/or isatoic anhydride derivative. The instructions can be included as an insert, incorporated into the container and/or in the packaging of the kit.

Another aspect of the present disclosure includes isatoic anhydrides that can be used as isobaric multiplexing reagents. As such, the multiplex isatoic anhydrides have one or more deuterium atoms substituted for one or more hydrogen atoms. Such reagents have several advantages over current commercially available multiplexing agents. For example, the multiplex isatoic anhydrides of the present disclosure can be water soluble and react with substrates very quickly, e.g., within minutes. The multiplex isatoic anhydrides of the present disclosure are fluorescent, due to the isatoic structure and can potentially increasing sample throughput if a fluorescence detector is included with the instrumentation. The multiplex isatoic anhydrides of the present disclosure can include an 8-plex, 16-plex and a 24-plex system and higher systems. The multiplex isatoic anhydrides of the present disclosure can also be used to label nucleic acids for multiplex analysis as well.

The multiplex isatoic anhydrides of the present disclosure are based on deuterium incorporation, which advantageously tends to be more cost effective. Moreover, the multiplex isatoic anhydrides of the present disclosure can be readily prepared. In certain embodiments, the multiplex isatoic anhydrides of the present disclosure can also include an N-substituent which includes a quaternary ammonium group. Such multiplex isatoic anhydrides advantageously have a constitutive charge in the label to mitigate the dipole change on going from hydrogen to deuterium. And can rely on hydrophilic. interaction chromatography (HILIC) to help mitigate chromatographic separations associated with the dipole change.

The multiplex isatoic anhydrides of the present disclosure can be useful for other high throughput screening technologies besides LC-MS/MS. For example, the multiplex. isatoic anhydrides of the present disclosure can be useful for other separation technologies coupled to an MS/MS system such a Capillary Electrophoresis or ion chromatography.

In addition, the multiplex isatoic anhydrides of the present disclosure are inherently fluorescent (excitation/emission approximately 340 nm/420 nm) thus facilitating the analysis and throughput. Changes in the fluorescent trace can readily aid in the identification of both significant and physiochemically relevant changes in the proteome, for example. Further peaks not exhibiting the characteristic fluorescence need not be analyzed by MS/MS thus leading to a reduction in the time required for analysis.

The fluorescent signature of the multiplex isatoic anhydrides of the present disclosure can readily facilitate electrophoretic separations of biomolecules in applications such as two-dimensional fluorescence difference gel electrophoresis (2D-DIGE). In such applications, the fluorescent signature facilitates the identification of in-gel separated biomolecules and the differences in such for comparisons among samples. Following excision, the labeling reagent isotopically encoded pattern can be used to quantify the differences in expression among the samples.

Such multiplex isatoic anhydrides can be represented by the following formula:

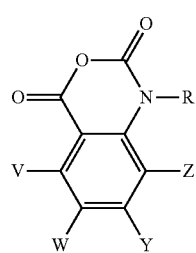

(V)

R represents an organo substituent having one or more hydrogen atoms substituted by one or more deuterium atoms. The variables V, W, Y, and Z represent the same substituents as described for the derivatives of Formula (I) herein including all of the various combinations and sub-combinations of each of the various variables. For example, V, W, Y, and Z independently represent H; $N_3$ (azido); $NO_2$ (nitro); amino; alkylamino; dialkylamino; branched or linear alkyl, e.g., a $C_{1-8}$ alkyl such as methyl, ethyl, propyl, isopropyl; branched or linear alkenyl, e.g., a $C_{1-8}$ alkenyl such as vinyl; branched or linear alkynyl, e.g., a $C_{1-8}$ alkynyl such as acetylenyl (—C≡CH); branched or linear alkoxy, such as methoxy, ethoxy; formyl (—CHO), acetyl (—COR$_5$), halide such as fluoro, chloro, bromo, iodo. $R_5$ represents $C_{1-8}$ aliphatic, which can be linear, branched, acyclic, cyclic, saturated or unsaturated. Aliphatic groups herein include linear, branched, acyclic, cyclic, saturated or unsaturated.

In one aspect of the present disclosure, the multiplex isatoic anhydride can have an N-substituent which includes a quaternary ammonium group. Such an anhydride can have the following formula:

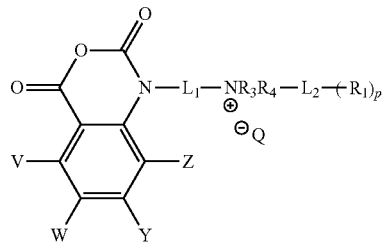

(VI)

The variables V, W, Y, Z, represent the same substituents as described for the derivatives of Formula (V) above including all of the various combinations and sub-combinations of each of the various variables. $L_1$ represents a linker group; $R_3$ and $R_4$ independently represent a linear or branched alkyl, an alkyl ether, or together form a cyclic heteroalkyl, or cyclic heteroaryl; $Q^-$ represents an anion; p is an integer from 0 to 2; when p is 0, $L_2$ represents a pendant organo group; when p greater than 0, $L_2$ represents a second independent linker group; $R_1$ represents an organo group; provided that at least one of $L_1$, $R_3$, $R_4$, $L_2$, or $R_1$ includes one or more deuterium atoms substituted for one or more hydrogen atoms.

Embodiments of the various groups for formula (VI) include, for example, where $L_1$ represents a linker group, e.g., a di-radical organo group between the two nitrogen atoms. $R_3$ and $R_4$ independently represent a linear or branched alkyl, e.g., a $C_{1-8}$ alkyl such as methyl, ethyl, n-propyl, n-butyl, etc., an alkyl ether; or together form a cyclic heteroalkyl, such as a pyrrolidinyl, piperidinyl, morpholinyl, piperazinyl; or cyclic heteroaryl, such as pyridinyl, imidazoyl, etc. $Q^-$ represents an anion such as a halide, e.g., a fluoro, chloro, bromo, or iodo anion, a sulfonate, sulfate, or carboxylate anion. The variable p is an integer from 0 to 2, e.g., p can be 0, 1, or 2. When p is 0, the multiple isatoic anhydride does not include an $R_1$ group and $L_2$ represents a pendant organo group on the quaternary amine nitrogen. If $R_1$1 is not present then at least of $L_1$, $R_3$, $R_4$, or $L_2$ includes one or more deuterium atoms substituted for one or more hydrogen atoms. When p is greater than 0, $R_1$ is present and $L_2$ represents a second independent linker group, e.g., a di-radical organo group between the quaternary nitrogen and one or more $R_1$ groups. When p is 2, there are two $R_1$ groups on the multiplex isatoic anhydride, which can be the same or different. For each of the various embodiments, at least one of $L_1$, $R_3$, $R_4$, $L_2$, or $R_1$ includes one or more deuterium atoms substituted for one or more hydrogen atoms.

As linker groups, $L_1$ and $L_2$ independently represent a di-radical organo group, e.g., a di-radical $C_{1-60}$ organo, which can be aliphatic or aromatic or include elements of both. The di-radical organo group can include heteroatoms along the main chain and/or substituents. As a pendant group, $L_2$ represents a pendant organo group, e g., a pendant $C_{1-60}$ organo group, which can be aliphatic or aromatic or include elements of both. The pendant group can include heteroatoms along the main chain and/or substituents. Hereroatoms (HA) along the main chain of the linker di-radical or pendent organo group can include one or more of: —CO—, —C(O)X—, —XC(O)—, —X—, —S—, —S(O)—, —XS(O)$_2$—, —S(O)$_2$X—, wherein X is O, S, NH, or NR$_5$ provided that if X is —NH—, the secondary amine does not substantially react with the anhydride of the isatoic anhydride derivative. That is, the secondary amine is not basic by virtue of having an electron withdrawing substituent such as an aryl group or a secondary amine substituted with a dinitrophenyl. The di-radical organo group or pendent organo group having heteroatoms along the main chain include polyethers, e.g., polyethylene glycol, polypropylene glycol, poly(tetramethylene oxide) (also referred to as a polytetrahydrofuran), polyesters, polyamides, ethyloxazolines, etc. In addition, the di-radical organo group or pendent organo group of $L_1$ and $L_2$ can independently include substituents on or off the main chain such as an alkyl, aryl, alkoxy, thioether, amide, halide, etc.

If present, $R_1$ can represent a deuterated alkyl, aryl, e.g., phenyl, or alkyl aryl, for example.

In an embodiment of the present disclosure, multiplex isatoic anhydrides can be selected from the following compounds.

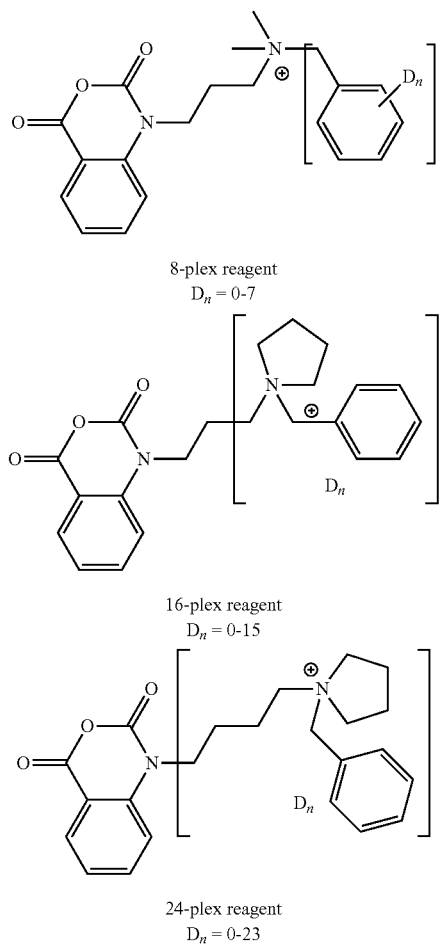

The multiplex isatoic anhydrides shown above can have up to 23 deuterium atoms substituted in a single isatoic anhydride. The bracketed groups can have the number of substituted deuterium noted by the symbol $D_n$. For example deuterium can be substituted on the anhydride with the $D_{0-7}$ coming from deuterated toluene derivatives and the $D_8$ coming from THF d-8. Examples of 8-plex, 16-plex and 24-plex are shown above.

Figure 10A:
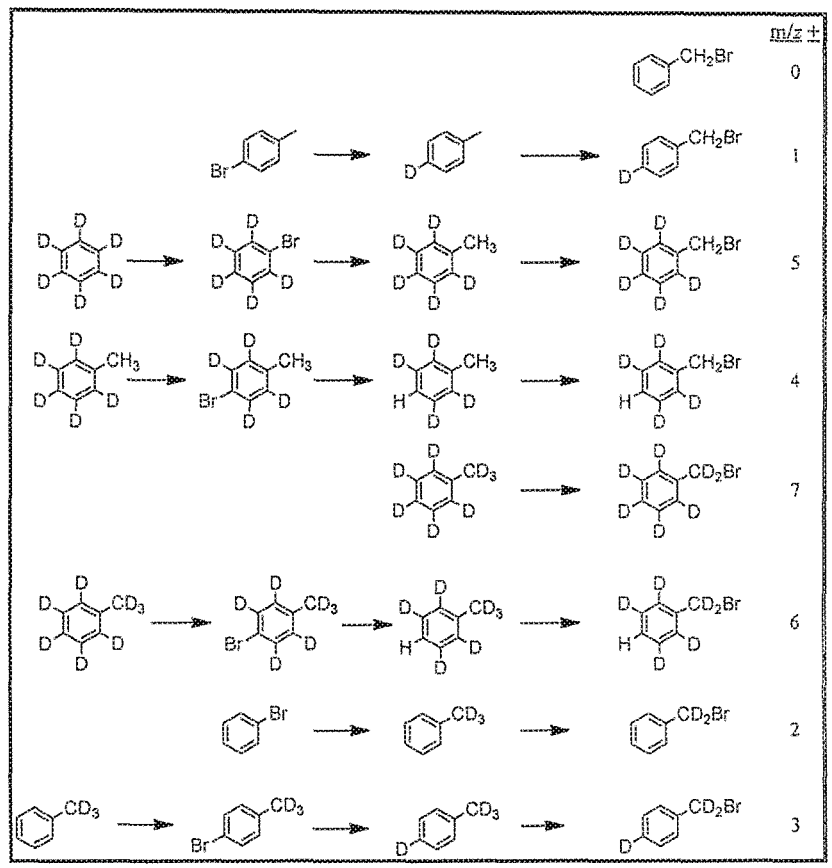
FIGS. 10A, 10B and 10C are schemes showing the preparation of multiplex isatoic anhydrides in accordance with embodiments of the present disclosure.
Figure 10B:
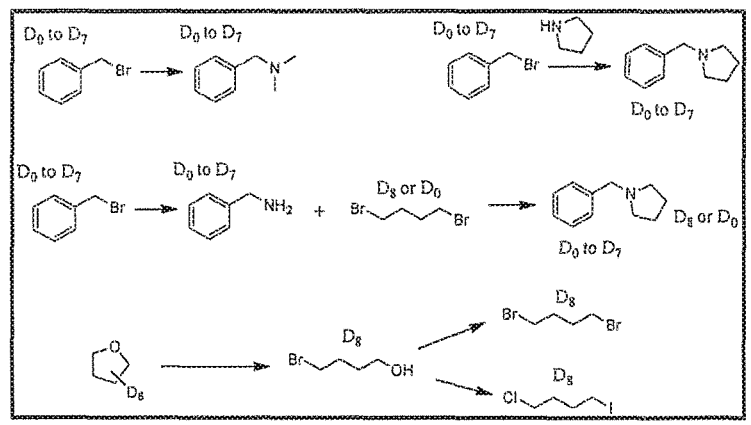

The isatoic anhydride derivatives of the present disclosure can be readily prepared from common starting materials. For example, the multiplex isatoic anhydrides can be prepared generally according to the schemes shown in FIGS. 10A and 10B. FIG. 10A shows a scheme for preparing D0 to D7 isotopes, while FIG. 10B shows a scheme for preparing the pieces for the multiplex reagents from deuterated solvents.

Figure 10C:
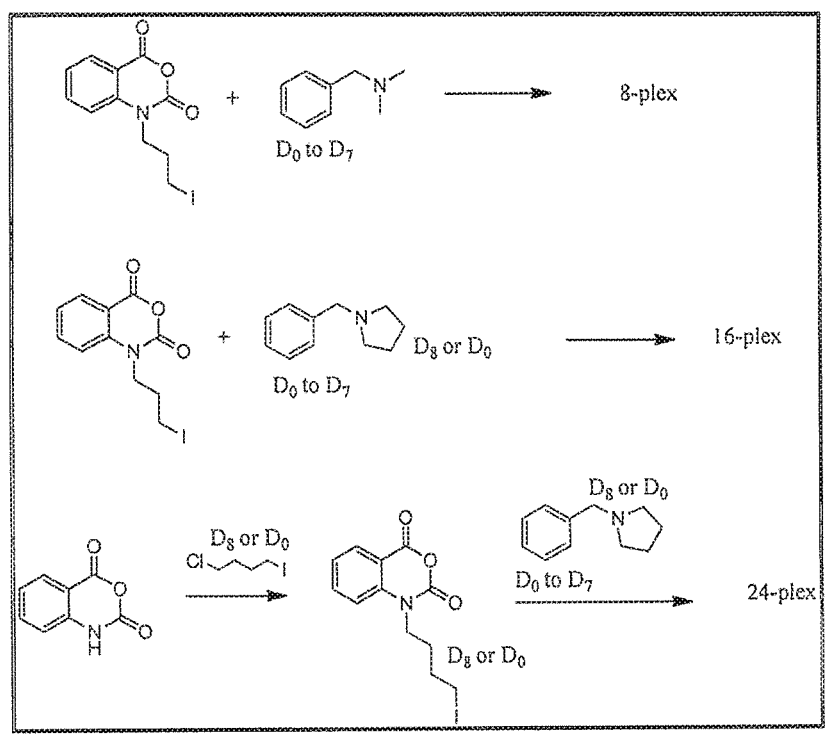

As shown in the scheme of FIG. 10C, multiplex isatoic anhydrides can be prepared by reacting an isatoic anhydride amine with a Q-$L_2$-($R_1$)p compound. The procedures shown in the schemes of FIGS. 10A-10C offer versatile processes for preparing the multiplex isatoic anhydrides of the present disclosure.

EXAMPLES

The following examples are intended to further illustrate certain preferred embodiments of the disclosure and are not limiting in nature. Those skilled in the art will recognize, or be able to ascertain, using no more than routine experimentation, numerous equivalents to the specific substances and procedures described herein.

Compounds 1a to 1d were prepared according to general Scheme 8 and the general procedure described below.

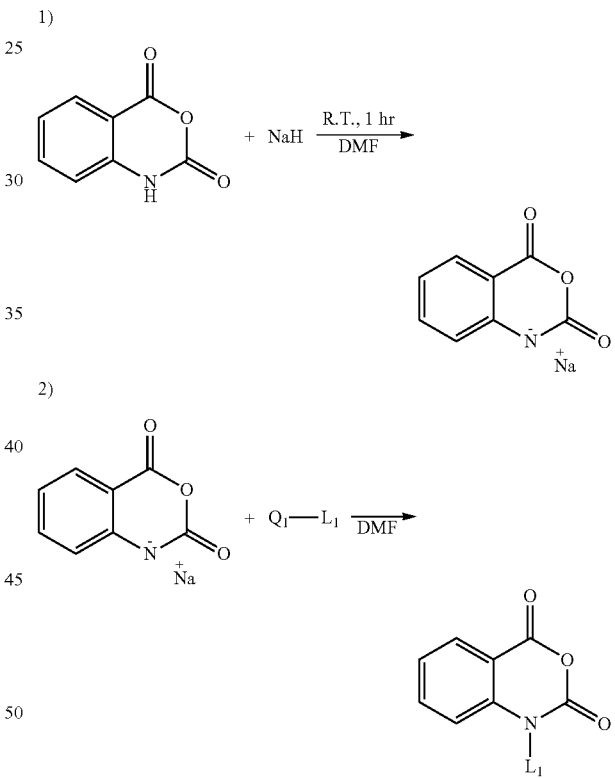

TABLE 9

| Reagent $L_1$—$Q_1$ or $R_3R_4NL_1$—$Q_1$ | Compound | $L_1$ or $R_3R_4NL_1$ | Yields (%) (recrystallized) |
|---|---|---|---|
| Me$_2$H$\overset{\oplus}{N}$—CH$_2$CH$_2$Cl Cl$^{\ominus}$ | 1a | Me$_2$N—CH$_2$CH$_2$ | 28 |
| [piperidinium-CH$_2$CH$_2$-Cl, Cl$^{\ominus}$] | 1a' | [piperidine]—CH$_2$CH$_2$ | 92 |

TABLE 9-continued

| Reagent L₁—Q₁ or R₃R₄NL₁—Q₁ | Compound | L₁ or R₃R₄NL₁ | Yields (%) (recrystallized) |
|---|---|---|---|
| I—CH₂CH₂CH₂Cl | 1b | I—CH₂CH₂CH₂ | 58 |
| Br—CH₂CH₂Br | 1c | BrCH₂CH₂ | 35 |
| Br—CH₂CH₂CH₂—Br | 1d | Br—CH₂CH₂CH₂ | 25 |

General procedure for the synthesis of isatoic anhydride derivatives 1a-d: To a Schlenk flask under dry nitrogen (N₂) was added (1.5 g, 36 mmol) 60 wt % sodium hydride in mineral oil (NaH) (1a & 1a' shown in the table above required 2 equivalents of NaH). To this was added 15 ml of dry hexanes, the suspension briefly stirred then allowed to settle, and the hexanes removed via cannula. This process was repeated three times. To the freshly rinsed NaH was added anhydrous dimethylformamide (DMF) (30 ml) at room temperature resulting in a cloudy suspension. To this suspension was added isatoic anhydride (5.1 g, 30 mmol) in one portion. Following this addition, an additional 20 ml of anhydrous DMF was added and the resulting suspension was stirred for 60 minutes, upon which time a substituted alkyl halide (L₁-Q₁ shown in the table above) was added (36 mmol) in one portion. The resulting suspension was stirred for approximately 18 hours yielding a clear and colored solution containing the desired product. The resulting solution was concentrated under vacuum at about 100° C. resulting in a darkly colored viscous residue. This residue was then dissolved into dichloromethane (150 ml) and extracted three times with 100 ml of saturated sodium bicarbonate (NaHCO₃) (aq). Finally the organic layer was washed one time with 100 ml of brine solution. The organic layer was then collected and stirred with activated carbon (0.5 g) for 30 minutes. The resulting organic solution was then filtered through a plug of magnesium sulfate (MgSO₄) to both remove the activated carbon and dry the solution of residual water. The resulting solution was then concentrated under vacuum to remove the dichloromethane resulting in a lightly colored solid that was then recrystallized from isopropanol.

Derivatives 1n to 1s were prepared according to Scheme 9 and the general procedure described below.

Scheme 9

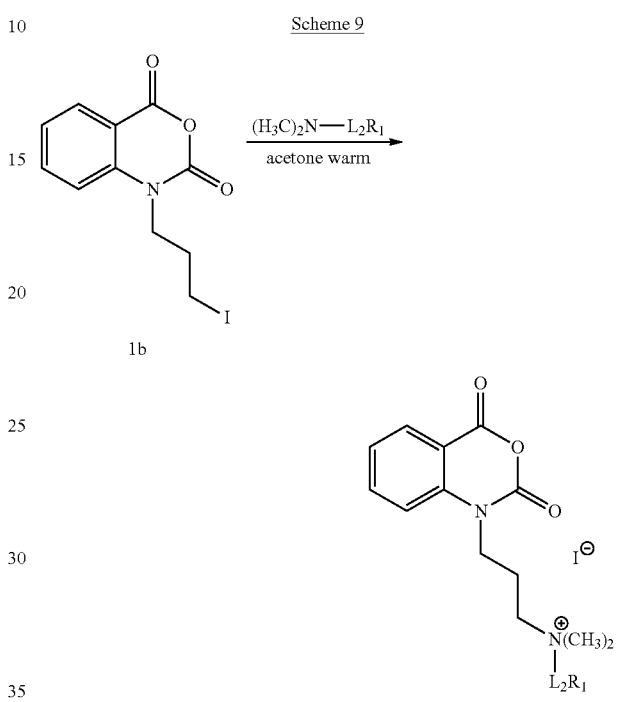

TABLE 10

| Reagent (CH₃)₂N—L₂R₁ | | L₂R₁ | Yield (%) |
|---|---|---|---|
| 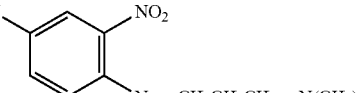 (CAS #25238-52-2) | 1n | 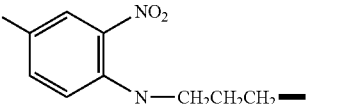 | 44 |
| 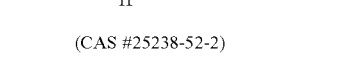 (CAS #38711-20-5) | 1o |  | 65 |
| 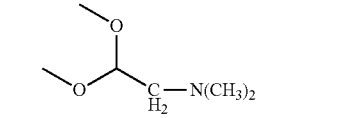 Prepared from the 4-azidobenzoic acid (CAS #6427-66-3) by reacting without thionyl chloride followed by Me₂N(CH₂)₂NH₂ | 1p | 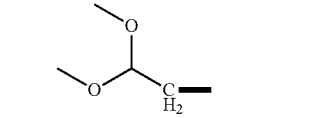 | 72 |

TABLE 10-continued

| Reagent (CH$_3$)$_2$N—L$_2$R$_1$ | | L$_2$R$_1$ | Yield (%) |
|---|---|---|---|
| isobutyryl thioester with Me$_2$N(CH$_2$)$_2$S— linker<br>Prepared from Me$_2$N(CH$_2$)$_2$SH and isobuytryl chloride | 1p' | (CH$_3$)$_2$CHC(O)S—CH$_2$CH$_2$— | 65 |
| 4-(trifluoromethyl)-N-(2-(dimethylamino)ethyl)benzamide<br>(CAS #247907-45-5) | 1q | 4-CF$_3$-C$_6$H$_4$-C(O)NH—CH$_2$CH$_2$— | 44 |
| isopropylidene hydrazide derivative<br>(CAS #687604-33-7) | 1r | (CH$_3$)$_2$C=N-NH-C(O)-CH$_2$— | 58 |
| biotin amide derivative<br>(CAS #372170-34-8) | 1s | biotinyl-NH—CH$_2$CH$_2$CH$_2$— | 95 |

General procedure for the synthesis of isatoic anhydride derivatives from 1b. To a 3 ml screw capped vial containing 1b (about 99 mg, 0.3 mmol) was added 1 ml of reagent grade dry acetone. The mixture was heated to dissolve the reagent followed by filtration through a 0.4 µm syringe filter to remove any insoluble amino acid (from hydrolysis of 1b). To this solution was added the corresponding nucleophile (CH$_3$)$_2$N-L$_2$R$_1$ (shown in the table above) (0.3 mmol) and the solution was allowed to stand for 18 hours at 40° C. Most final products were solids and generally isolated by suction filtration. Products were verified by NMR and ESI mass spectrometry. The crystalline products were pure by NMR analysis except for traces of acetone. When no solid precipitate was observed, NMR and ESI mass spectrometry of the reaction mix was used to confirm the product formation. In the $^1$H NMR, the methyl hydrogen's on the nitrogen of the amine are diagnostic. These hydrogen resonances in the starting amine (CH$_3$)$_2$N-L$_2$R$_1$ are at about 2.2 ppm while the corresponding hydrogens of the product (methyls on the quaternized amine) are between 3.1 and 3.3 ppm. Compound 1s did not crystallize in the solvents used and was obtained as a viscous oil after removing the solvent with rotary evaporation. NMR analysis showed 1s to be greater than 95% pure by this procedure.

Derivatives 1t to 1aa were prepared according to general Scheme 10 and the general procedure described below.

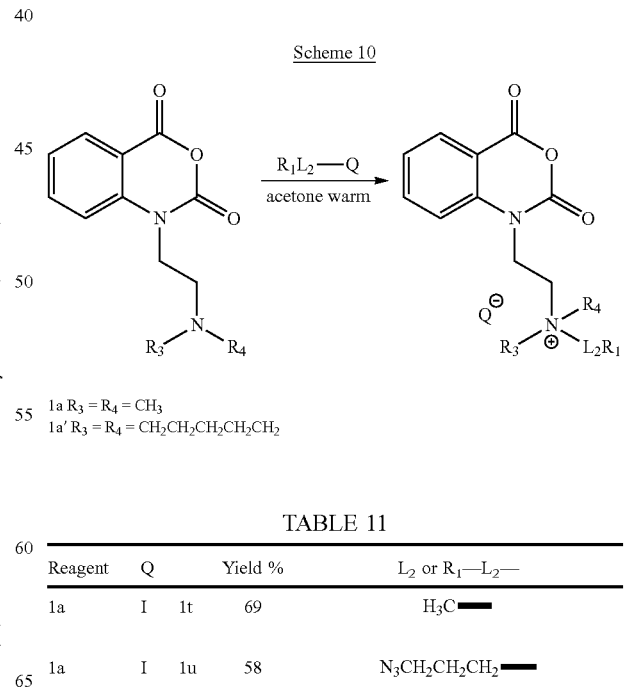

Scheme 10

1a R$_3$ = R$_4$ = CH$_3$
1a' R$_3$ = R$_4$ = CH$_2$CH$_2$CH$_2$CH$_2$CH$_2$

TABLE 11

| Reagent | Q | | Yield % | L$_2$ or R$_1$—L$_2$— |
|---|---|---|---|---|
| 1a | I | 1t | 69 | H$_3$C— |
| 1a | I | 1u | 58 | N$_3$CH$_2$CH$_2$CH$_2$— |

TABLE 11-continued

| Reagent | Q | | Yield % | L₂ or R₁—L₂— |
|---|---|---|---|---|
| 1a | Br | 1v | 62 | $CH_2=CHCH_2$— |
| 1a | Br | 1w | 59 | $HC\equiv CCH_2$— |
| 1a' | Br | 1w' | 72 | $HC\equiv CCH_2$— |
| 1a | Br | 1x | 75 | 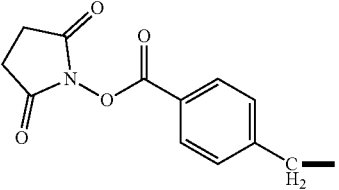 |
| 1a | Br | 1y | 53 | 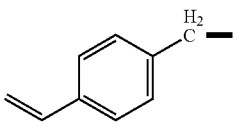 |
| 1a | I | 1z | 61 | $CH_3$—$(CH_2)_{16}$—$CH_2$— |
| 1a | Br | 1aa | 45 | 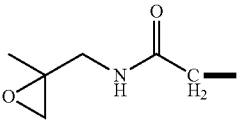 |

General procedure for the synthesis of isatoic anhydride derivatives from 1a: To a 3 ml screw capped vial containing 1a (70 mg, 0.3 mmol) was added 1 ml of reagent grade dry acetone. The mixture was heated to dissolve the reagent then filtered through a 0.4 μm syringe filter to remove any insoluble amino acid (from hydrolysis of 1a). To this solution was added the corresponding nucleophile $QL_2R_1$ (shown in the table above) (0.3 mmol) and the solution was allowed to stand for 18 hours at 40 °C. These reactions were monitored by $^1H$ NMR; the methyl hydrogen's on the nitrogen of the amine are diagnostic. These hydrogen resonances in the starting material (1a) are at about 2.3 ppm while the corresponding hydrogens of the product are between 3.1 and 3.3 ppm. The final products were typically solids and isolated by suction filtration. The products were verified by NMR and ESI mass spectrometry. The products were generally pure except for traces of acetone. When no solid was observed, ESI mass spectrometry and NMR spectroscopy of the reaction mix was used to confirm product formation. If the product could not be induced to crystallize, the solvent was removed by rotary evaporation to leave a viscous oil. The yield was determined by the crude weight and the purity by NMR.

Relative Reactivity of Anhydride and a Chemically Reactive $R_1$ Group

Isatoic anhydride derivative 1aa is a dual electrophilic reagent with both the reactive ends (the anhydride and the epoxide) being reactive towards amines. Rapid injection NMR experiments with this reagent show that there is a dramatic difference in the rate of reaction at the two ends. The reaction with 1 equivalent of n-butylamine (a model for the basic amine in a lysine residue of a protein) in $D_2O$ buffered to pH of 8.4, with sodium bicarbonate, showed that the amine reacts with the anhydride function with no observable reaction with the epoxide group.

Isatoic anhydride derivative 1x is also a dual electrophilic reagent with both reactive ends (the anhydride and the NHS ester) being reactive towards amines. NMR kinetic studies with this reagent with 1 equivalent of n-butylamine show that the reaction rates are similar for both ends. However, the substituents on the aryl ring (V, W, X, Y) allow for tuning the relative reaction rates. For example, making V a bulky alkyl group is expected to slow the rate of reaction at the anhydride moiety relative to the NHS ester. Alternatively, making W or X electron withdrawing is expected to increase the rate of reaction at the anhydride relative to the NHS ester.

Labeling of Bovine Serum Albumin

Isatoic anhydride derivative 1w was used to label bovine serum albumin according to Scheme 11 and the procedure described below.

Scheme 11

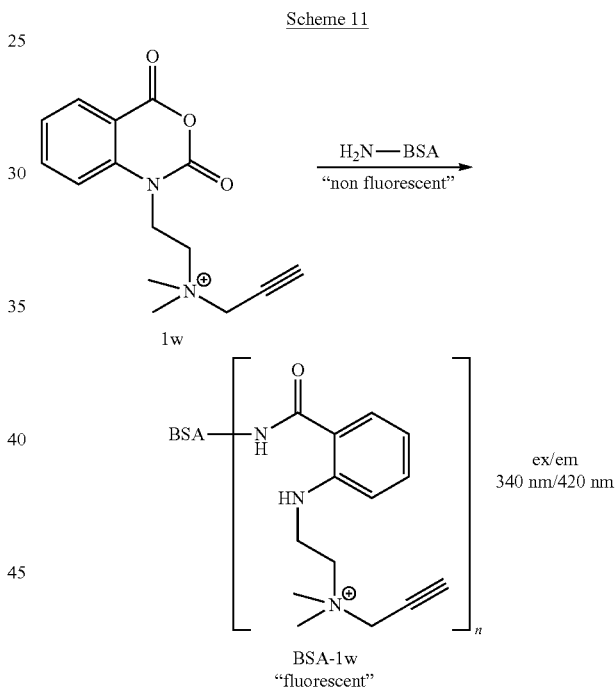

Figure 4:
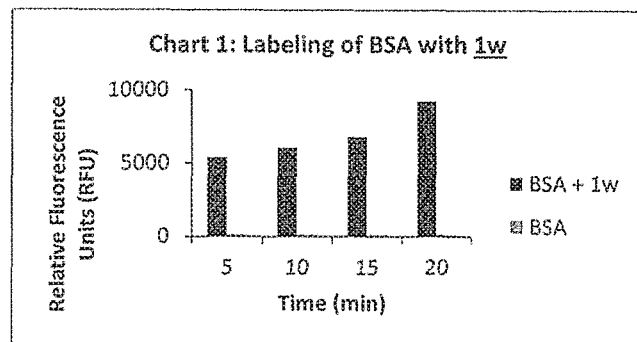
FIG. 4 is a chart showing the relative fluorescence over time of a bovine serum albumin labeled with an isatoic anhydride derivative of the present disclosure.

To a 40 mg/ml solution (50 μl) of bovine serum albumin (BSA) in 5 mM sodium bicarbonate (pH 8.4 and 25° C.) was added 50 μl of 1w (1 mg/ml in DI $H_2O$). Immediately this solution was monitored for fluorescence over 20 min using peak excitation emission wavelengths of 350 ex/420 em respectively. FIG. 4 is a chart showing the relative fluorescence of labeled BSA over time which corresponds to the incorporation of alkynes into the BSA. This product would be ready for attachment to a complimentary azide functionality on another molecule to couple them together using an azide-alkyne click reaction.

Labeling of DNA Aptamer

Isatoic anhydride derivative 1p was used to label DNA Aptamer with an 5' $NH_2$ primer according to Scheme 12 and the procedure described below.

Scheme 12

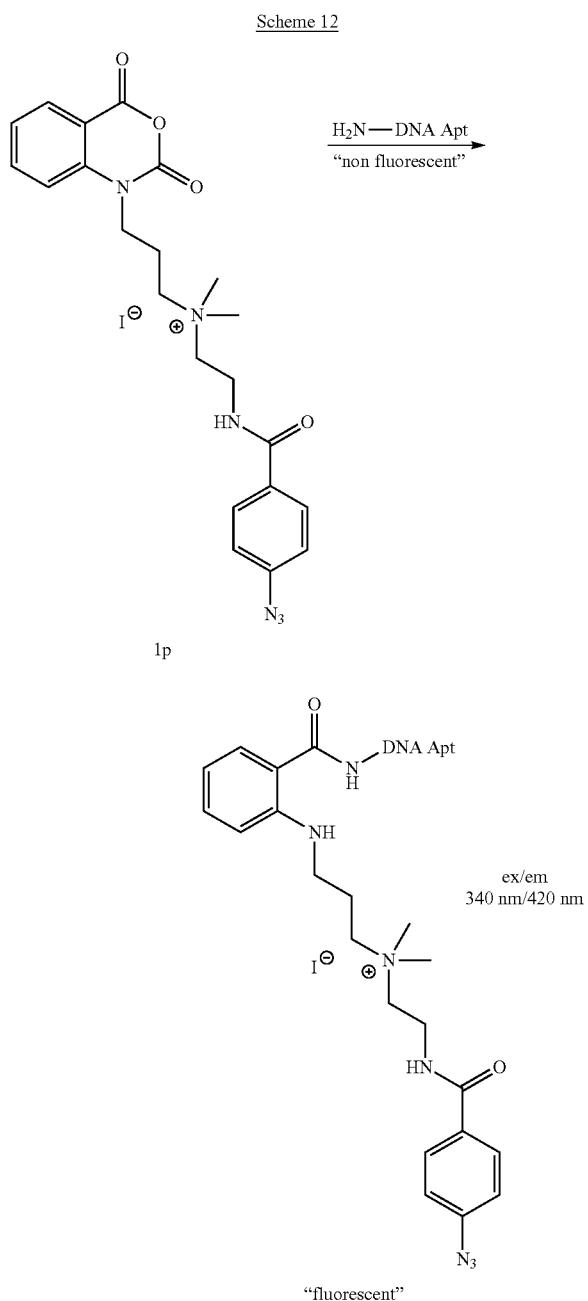

Figure 5:
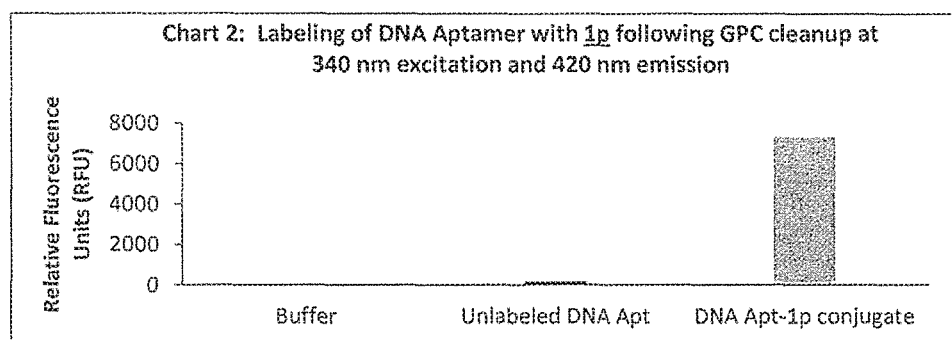
FIG. 5 is a chart showing the relative fluorescence of a buffer, unlabeled DNA Aptamer and a DNA Aptamer labeled with an isatoic anhydride derivative, through an amine primer on the DNA, of the present disclosure.

To a 1 mg/ml solution (50 µl) of DNA Aptamer (DNA Apt) in 5 mM sodium bicarbonate (pH 8.4 and 25° C.) was added 50 µl of 1p (1 mg/ml in DI H₂O). The resulting solution was left to incubate for approximately 5 min at 25° C. upon which time the DNA Apt-1p was cleaned of hydrolyzed and unreacted 1p by gel permeation chromatography (GPC) (Princeton Separations CS-10). The purified DNA Apt-1p bioconjugate was then measured for fluorescence using peak excitation/emission wavelengths of 350 nm/420 nm respectively. The fluorescence of the DNA Apt-1p bioconjugate was compared directly with unlabeled DNA Apt as shown in FIG. 5, which demonstrates that the azide has been incorporated onto the DNA. This azide conjugate is ready to be coupled with alkyne partner in an azide-alkyne click reaction to couple the two complimentary partners together.

Labeling and Conjugating Bovine Serum Albumin and Human Insulin

Isatoic anhydride derivative 1w and 1q were used to label bovine serum albumin (BSA) and human insulin according to the schemes shown in FIG. 6 and the procedures described below.

Figure 6:
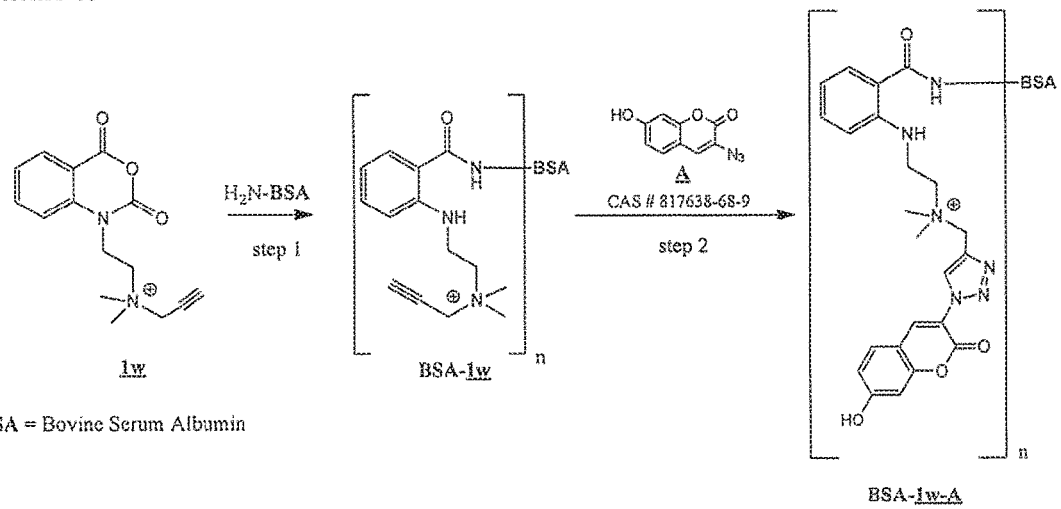
FIG. 6 illustrates schemes for labeling and conjugating bovine serum albumin and insulin with an isatoic anhydride derivative of the present disclosure.
Figure 6:
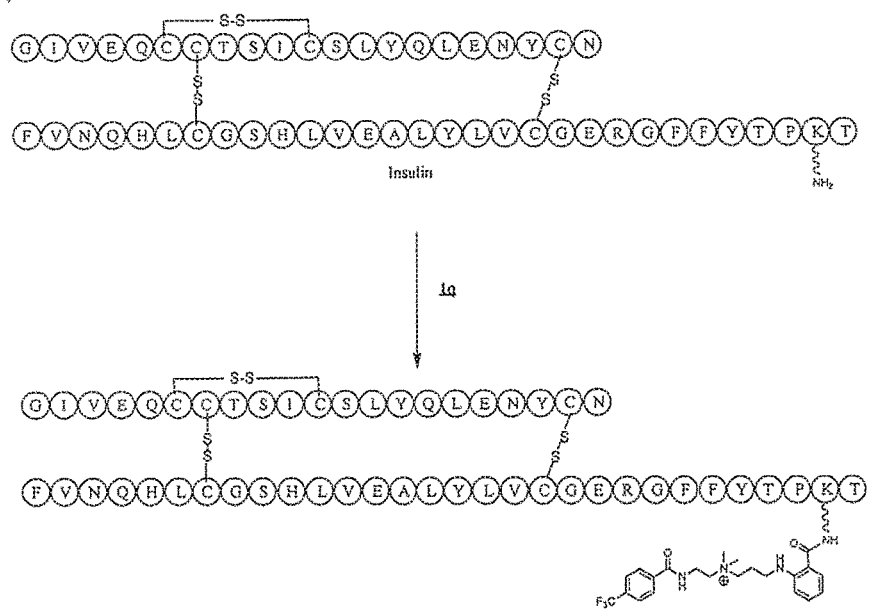
Figure 7:
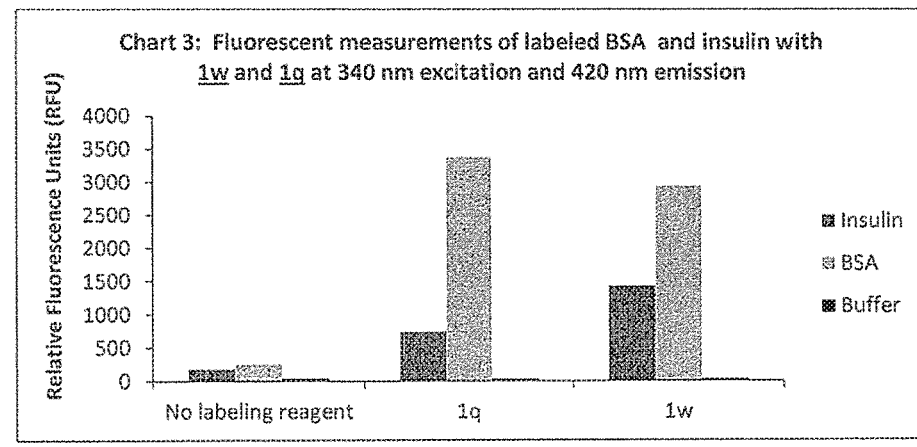
FIG. 7 is a chart showing the relative fluorescence of unlabeled reagents and labeled bovine serum albumin and insulin with an isatoic anhydride derivative of the present disclosure.

To a 20 mg/ml solution (50 µl) of bovine serum albumin (BSA) in 5 mM sodium bicarbonate (pH 8.4 and 25° C.) was added 50 µl of 1w (1 mg/ml in DI H₂O), (step 1; of the Scheme 13 in FIG. 6). The resulting solution was left to incubate for approximately 5 min at room temperature upon which time the BSA-1w conjugate was cleaned of hydrolyzed and unreacted 1w by Gel permeation chromatography (GPC) (Princeton Separations CS-10). The purified BSA-1w conjugate was then analyzed for fluorescence using peak excitation emission wavelengths of 340 ex/420 em respectively, FIG. 7. The fluorescence measurement was compared to unlabeled BSA (10 mg/ml) using the same excitation/emission wavelengths. Minimal background fluorescence due to the buffer was observed.

To a 20 mg/ml solution (50 µl) of human insulin (manufacturer) in an 80:20 solution of 5 mM sodium bicarbonate (pH 8.4 and 25° C.): dimethyl sulfoxide (DMSO), was added 50 µl of 1w (1 mg/ml in DI H₂O). The resulting solution was left to incubate for approximately 5 min at room temperature upon which time the insulin-1w conjugate was cleaned of hydrolyzed and unreacted 1w by Gel permeation chromatography (GPC) (Princeton Separations CS-10). The purified insulin-1w conjugate was then analyzed for fluorescence using peak excitation emission wavelengths of 340 ex/420 em respectively, FIG. 7. The fluorescence measurement was compared to unlabeled insulin (10 mg/ml) using the same excitation/emission wavelengths. Minimal background fluorescence due to the buffer was observed. This procedure was repeated for the labeling of insulin with 1q. See FIG. 6, Scheme 14. NMR DOSY experiments were able to show that the fragment with the $CF_3$ group had the same diffusion rate as insulin showing that 1q is conjugated to insulin. These experiments show that bath an alkyne and a fluorous group can be incorporated into insulin. The insulin-1w conjugate is the coupling partner for an azide in azide-alkyne click reaction, while the insulin-1q conjugate demonstrates the ability to modify a molecule with a fluorous portion.

Coupling a Second Material to the BSA-1w Anthranilate

The BSA-1w anthranilate prepared above was further derivatized by a copper catalyzed 1,3-dipolar cycloaddition of BSA-1w with compound A according to Scheme 13, step 2, of FIG. 6 and the procedure described below.

Figure 8:
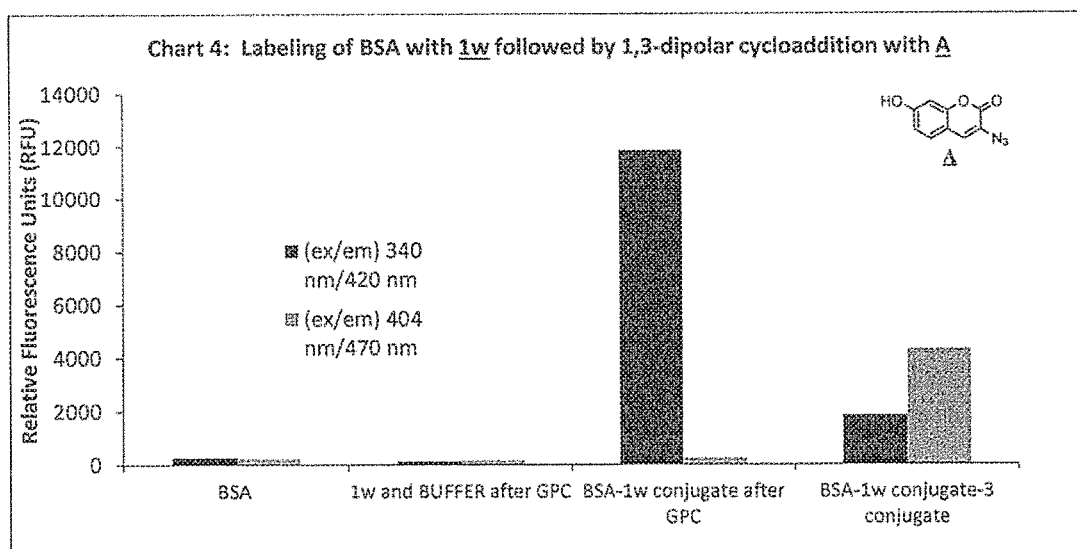
FIG. 8 is a chart showing the relative fluorescence of a conjugated bovine serum albumin after a 1,3-dipolar cycloaddition.

To a 40 mg/ml solution (50 µl) of bovine serum albumin (BSA) in 5 mM sodium bicarbonate (pH 8.4 and 25° C.) was added 50 µl of 1w (2 mg/ml in DI H₂O) and the resulting solution let sit to incubate at room temperature over 30 min. Following this, 50 µl of the solution was cleaned of hydrolyzed and unreacted 1w by gel permeation chromatography (GPC) (Princeton Separations CS-10). Labeling of BSA was confirmed by fluorescence (see FIG. 4) using peak excitation/emission wavelengths of 340 nm/420 nm respectively. Following the labeling of BSA with 1w, an optimized fluorogenic copper catalyzed azide-alkyne cycloaddition was performed according to the method of Hong et al., "Analysis and Optimization of Copper-Catalyzed Azide-Alkyne Cycloaddition for Bioconjugation" Angew Chem. Int. Ed. Engl. 2009:48(52):9879-9883. This method was selected as it is compatible with a wide assortment of biomolecules, is fast, and the progress of the reaction monitored by fluorescence resulting from formation of BSA- 1w-A. Briefly; 25 μl of BSA-1w (20 mg/ml) was added to 407.5 μl of phosphate buffer (100 mM, pH 7), 10 μl of A, 2.5 μl CuSO4 (20 mM in DI H$_2$O), 5.0 μl of Tris(3-hydroxypropyltriazolylmethyl)amine (THTPA) (50 mM in deionized H$_2$O), sodium ascorbate (100 mM in deionized H$_2$O), and aminoguanidine hydrochloride (100 mM in deionized H$_2$O). The resulting solution was left to incubate for 60 min at room temperature excluded from light. The click reaction was monitored by fluorescence using peak excitation/emission wavelengths of 340 nm/420 nm and 404 nm/470 nm respectively, FIG. 8. This sequence shows, using fluorescence, that the alkyne once in place on the biomolecule using 1w can be used in the azide-alkyne click reaction.

Labeling and Functionalizing of Nanoparticles

Isatoic anhydride derivative 1w was used to label and functionalize nanoparticles (NPs) composed of poly(lactic-co-glycolic acid) (PLGA) according to the following procedure.

Figure 9:
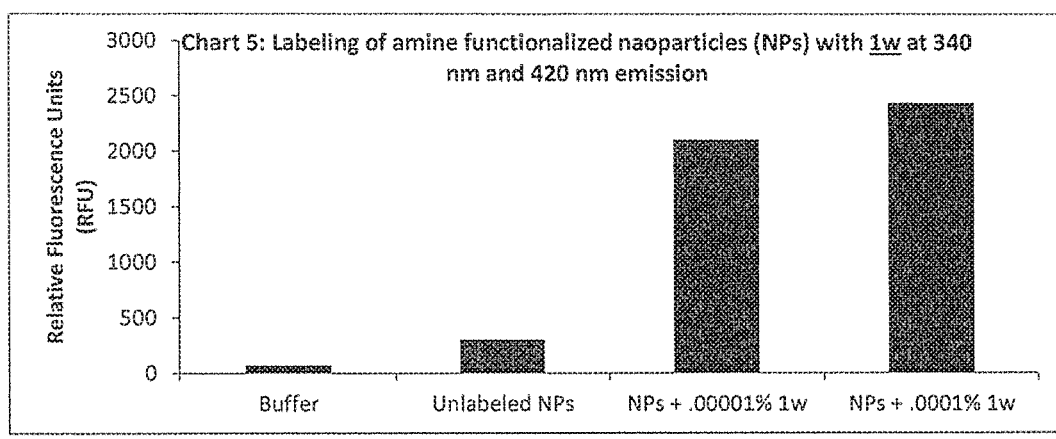
FIG. 9 is a chart showing the relative fluorescence of an amine functionalized nanoparticle conjugated with an isatoic anhydride derivative of the present disclosure.

10 mg of nanoparticles (NPs), functionalized with a primary amino group on the surface (at 0.00001 and 0.0001% amine functionality by wt %), were each added to separate 1.5 ml micro-centrifuge tubes, then dispersed into 250 μl of deionized H$_2$O. To each of these was added 50 μl of 1w (1 mg/ml in deionized H$_2$O). The resulting solutions were left to incubate at room temperature for 30 min. Following this, the NP-1w conjugates were pelleted on a centrifuge at 21,000 ref at 4° C. to remove both hydrolyzed and unreacted 1w. The NP-1w pellets were then redispersed into 500 μl of deionized H$_2$O and pelleted again as above. This was repeated 3 times. Finally the cleaned NP-1w conjugates were dispersed into 1 ml of deionized H$_2$O and the fluorescence recorded using peak excitation/emission wavelengths of 340 nm/420 nm respectively, FIG. 9. The fluorescence observed (FIG. 9) with the nanoparticles is evidence of the alkyne attachment to the surface of the nanoparticles. The NP-1w can then be paired up with a molecule containing an azide to do azide-alkyne click chemistry to attach a molecule to the nanoparticle.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of modifying a material, the method comprising combining an isatoic anhydride derivative with a material to form either (i) a isatoic anhydride derivative including the material coupled through R$_1$ having the structure of Formula (II) or (ii) an anthranilate derivative having the material coupled through the anhydride of the isatoic anhydride derivative having the structure of Formula (III):

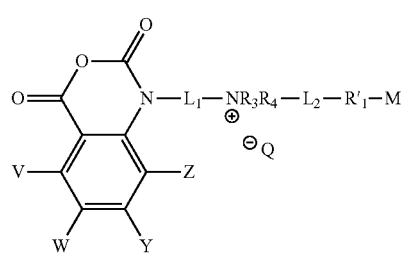

(II)

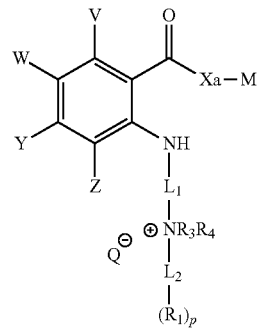

(III)

wherein M represents the material, Xa represents NH, NR$_5$, S, or O and R'$_1$ represents a group formed from the reaction or interaction of R$_1$ and the material M;

wherein the isatoic anhydride derivative has the following formula:

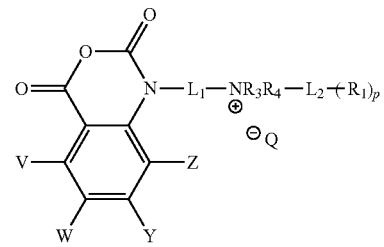

(I)

wherein V, W, Y, and Z individually represent H, N$_3$, NO$_2$, amino, alkylamino, dialkylamino, branched or linear alkyl, branched or linear alkenyl, branched or linear alkynyl, branched or linear alkoxy, branched or linear sulfenyl, an alkyne or azido substituted alkylamino, dialkylamino, alkyl, alkoxy, sulfenyl, formyl, acetyl, or halide; L$_1$ represents a linker group; R$_3$ and R$_4$ independently represent a linear or branched alkyl, an alkyl ether, or together form a cyclic heteroalkyl, or cyclic heteroaryl; Q$^-$ represents an anion; p is an integer from 0 to 2; when p is 0, L$_2$ represents a pendant organo group; when p greater than 0, L$_2$ represents a second independent linker group; R$_1$ represents a chemically reactive group, a binding group, or a detectable label.

2. The method of claim 1, comprising forming the anthranilate of Formula (III) wherein M is a biological material, p is 1 and R$_1$ is a chemically reactive group or a binding group.

3. The method of claim 1, comprising forming the anthranilate of Formula (III) wherein M is a biological material, p is 1 and R$_1$ is a detectable label.

4. The method of claim 1, comprising forming the anthranilate of Formula (III) wherein M is a polymeric nanoparticle.

5. The method of claim 1, further comprising coupling another material to the anthranilate of Formula (III) by coupling or binding the second material to R$_1$.

6. The method of claim 1, wherein V and Z are H and W and Y independently represents H, N$_3$, NO$_2$, NH$_2$, NHR$_5$, NR$_5$R$_5$, a C$_{1-6}$ alkyl, a C$_{1-6}$ alkenyl, a C$_{1-6}$ alkynyl, an alkyne or azido substituted NHR$_5$, NR$_5$R$_5$, C$_{1-6}$, OC$_{1-6}$, SC$_{1-6}$, —CHO or acetal; R$_3$ and R$_4$ independently represent a C$_{1-6}$ alkyl or together form a 5-6 membered ring heterocycle; R$_5$ represents C$_{1-8}$ aliphatic; Q$^-$ represents a halide anion; L$_1$ represents a di-radical $C_{1-60}$ organo; $L_2$ represents a di-radical $C_{1-60}$ organo when p is 1 and $L_2$ represents a pendant $C_{1-60}$ organo when p is 0.

7. The method of claim 1, comprising forming the anthranilate of Formula (III) and wherein p is 1; $R_1$ is a chemically reactive group; and M represents RNA, an RNA aptamer, DNA, a DNA aptamer, a protein, a peptide, an enzyme, a peptide aptamer, an antibody, or an antibody.

8. The method of claim 7, wherein each of V, Z, W and Y represent H.

9. The method of claim 7, wherein $L_1$ represents $R_5$; and $L_2$ represents —$(CH_2)n$-$(R_5O)m$-$R_5$; $R_5$ represents a $C_{1-8}$ aliphatic; n represents integers of 1 to 30; and m represents integers of 0 to 30.

10. The method of claim 7, wherein $R_3$ and $R_4$ independently represent a linear or branched $C_{1-8}$ alkyl.

11. The method of claim 7, wherein Q- represents a halide anion.

12. The method of claim 1, comprising forming the anthranilate of Formula (III) and wherein $L_1$ represents $R_5$; and $L_2$ represents —$(CH_2)n$-$(R_5O)m$-$R_5$; $R_5$ represents a $C_{1-8}$ aliphatic; n represents integers of 1 to 30; and m represents integers of 0 to 30; $R_3$ and $R_4$ independently represent a linear or branched $C_{1-8}$ alkyl; Q- represents a halide anion; p is 1; $R_1$ is a chemically reactive group; and M represents RNA, an RNA aptamer, DNA, a DNA aptamer, a protein, a peptide, an enzyme, a peptide aptamer, an antibody, or an antibody.

13. The method of claim 12, wherein M represents a peptide.

14. The method of claim 1, comprising forming the anthranilate of Formula (II).

15. The method of claim 14, wherein each of V, Z, W and Y represent H.

16. The method of claim 14, wherein $L_1$ represents $R_5$; and $L_2$ represents —$(CH_2)n$-$(R_5O)m$-$R_5$; $R_5$ represents a $C_{1-8}$ aliphatic; n represents integers of 1 to 30; and m represents integers of 0 to 30.

17. The method of claim 14, wherein $R_3$ and $R_4$ independently represent a linear or branched $C_{1-8}$ alkyl.

18. The method of claim 14, wherein Q- represents a halide anion.

19. The method of claim 1, comprising forming the anthranilate of Formula (II) and wherein $L_1$ represents $R_5$; and $L_2$ represents —$(CH_2)n$-$(R_5O)m$-$R_5$; $R_5$ represents a $C_{1-8}$ aliphatic; n represents integers of 1 to 30; and m represents integers of 0 to 30; $R_3$ and $R_4$ independently represent a linear or branched $C_{1-8}$ alkyl; Q- represents a halide anion; p is 1; $R_1$ is a chemically reactive group; and M represents RNA, an RNA aptamer, DNA, a DNA aptamer, a protein, a peptide, an enzyme, a peptide aptamer, an antibody, or an antibody.

20. The method of claim 19, wherein M represents a peptide.

* * * * *